(12) United States Patent
Andres et al.

(10) Patent No.: US 7,846,653 B2
(45) Date of Patent: *Dec. 7, 2010

(54) ASC AS A MARKER FOR COLORECTAL CANCER

(75) Inventors: Herbert Andres, Penzberg (DE); Marie-Luise Hagmann, Penzberg (DE); Johann Karl, Peissenberg (DE); Ursula Kunert, Munich (DE); Gabriele Pestlin, München (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 415 days.

This patent is subject to a terminal disclaimer.

(21) Appl. No.: 11/820,769

(22) Filed: Jun. 20, 2007

(65) Prior Publication Data

US 2009/0155820 A1  Jun. 18, 2009

Related U.S. Application Data

(63) Continuation of application No. PCT/EP2005/013869, filed on Dec. 22, 2005.

(30) Foreign Application Priority Data

Dec. 23, 2004  (EP)  .................................. 04030619
Apr. 20, 2005  (EP)  .................................. 05008660

(51) Int. Cl.
*C12Q 1/00*  (2006.01)
*G01N 33/574*  (2006.01)

(52) U.S. Cl. ............................. 435/4; 435/7.1; 435/7.23

(58) Field of Classification Search ........................ None
See application file for complete search history.

(56) References Cited

U.S. PATENT DOCUMENTS 6,911,306 B1 * 6/2005 Vertino ........................... 435/6

FOREIGN PATENT DOCUMENTS

| JP | 2004-198419 A | 7/2004 |
|---|---|---|
| WO | WO 2004/057336 A2 | 7/2004 |
| WO | WO 2004/104593 A1 | 12/2004 |
| WO | WO 2005/040806 A2 | 5/2005 |
| WO | WO 2006/066917 A2 | 6/2006 |

OTHER PUBLICATIONS

Yokoyama et al, Cancer Lett, vol. 202, p. 101-108, 2003.*
Bhatavdekar et al , Dis Colon Rectum vol. 44, p. 523-533, 2001.*
Ahlquist, D. et al., "Fecal Occult Blood Testing for Colorectal Cancer," Colorectal Neoplasia, Part II: Diagnosis & Treatment, vol. 26, No. 1, Mar. 1997, 41-55.
Conway, K. et al., "TMSI, a Novel Proapoptoticf Caspase Recruitment Domain Protein, Is a Target of Methylation-induced Gene Silencing in Human Breast Cancers," Cancer Research 60, 6236-6242, Nov. 15, 2000.
Duffy, M. et al., "Clinical Utility of Biochemical Markers in Colorectal Cancer: European Group on Tumour Markers (EGTM) Guidelines," European Journal of Cancer 49 (2003) 718-727.
Martell, R. et al., "OVX1 and CEA in Patients with Colon Carcinoma, Colon Polyps and Benign Colon Disorders," The International Journal of Biological Markers, vol. 13, No. 3, (1998) 145-149.
Masumoto, J. et al., "ASC, a Novel 22-kDa Protein, Aggregates during Apoptosis of Human Promyelocytic Leukemia HL-60 Cells," The Journal of Biological Chemistry, col. 274, No. 48, Nov. 26, 1999, 33835-33838.
Masumoto, J. et al., "Expression of Apoptosis-associated Speck-like Protein Containing a Caspase Recruitment Domain, a Pyrin N-terminal Homology Domain-containing Protein, in Normal Human Tissues," The Journal of Histochemistry and Cytochemistry, vol. 49(10) 1269-1275, 2001.
Nakata, B. et al., "Serum CYFRA 21-1 (cytokeratin-19 fragments) is a useful tumour marker for detecting disease relapse and assessing treatment efficacy in breast cancer," British Journal of Cancer (2004) 91, 873-878.
Shiohara, M. et al., "ASC, Which is Composed of a Pyrin-N-Terminal Homology Domain and a Caspase-Recruitment Domain, Is Up-Regulated by Inflammation and Apoptosis in Human Neutrophis," Blood, 98(2000) 229a.
Silvis, S. et al., "Endoscopic Complications," JAMA, Mar. 1, 1976, vol. 235, No. 9, 928-930.
Sturgeon, C. et al., "Practice Guidelines for Tumor Marker Use in the Clinic," Clinical Chemistry 48:8, 1151-1159 (2002).
Can der Gaast, A. et al., ,,Evaluation of a new tumour marker in patients with non-small-cell lung cancer: Cyfra 21.1, Br. J. Cancer (1994) 69, 525-528.
Yokoyama, T. et al., "Methylation of ASC/TMS1, a proapoptotic gene responsible for activating procaspase-1, in human colorectal cancer," Cancer Letters 202 (2003) 101-108.
Zweig, M. et al., "Receiver-Operating Characteristics (ROC) Plots: A Fundamental Evaluation Tool in Clinical Medicine," Clin, Chem. 39/4, 561-577 (1993).
Database UniProt (Online), EBI accession No. UNIPROT: Q9ULZ3, XP002365772, Oct. 16, 2001.
Notice of Grounds for Rejection (English Translation) of an Office Action issued Apr. 26, 2010 in Japanese Patent Application No. 2007-544847.
Kojima, Osamu et al., Igan, Daichogan Kanja ni okeru Kessei NSE no Shuyou Ma-ka- toshiteno Igi (Significance of Serum NSE Levels as Tumor Markers in Patients with Gastric and Colorectal Cancer), Rinsho Byori, 1986, pp. 1236-1240, vol. 34, No. 11, Japan.
Matsumoto, H. et al., Daichogan no Shuyokanryujomyakuketsu ni okeru CYRA21-1 Sokutei no Rinshoteki Igi—Tokuni Jutsugokekkoseisaihatsu no Koukiken-Inshi to shiteno Igi- (Clinical Significance of CYRA21-1 Assay in Mesenteric Veins of Colorectal Cancer—Particularly Significance as a High Risk Factor for Postoperative Hematogenous Metastasis-), Journal of Japan Society of Coloproctology, 2002, pp. 136-144, vol. 55, No. 3 , Japan (Abstract).
Miyashita, T. et al., Daichogan ni okeru Kessei CEA, CA19-9, CYFRA21-1, IAP Sokutei ni yoru combination assay no Rinshoteki Igi (Clinical Significance of Combination Assay of Serum CEA, CA19-9, CYFRA21-1, and IAP in Colorectal Cancer), Journal of the Japan Society of Coloproctology, 2000, pp. 76-82, vol. 53, No. 2.

* cited by examiner

*Primary Examiner*—Larry R. Helms
*Assistant Examiner*—Lei Yao

(57) ABSTRACT

The present invention relates to the diagnosis of colorectal cancer. It discloses the use of protein ASC (apoptosis-associated speck-like protein containing a caspase-associated recruitment domain) in the diagnosis of colorectal cancer. It relates to a method for diagnosis of colorectal cancer from a liquid sample, derived from an individual by measuring ASC in said sample. Measurement of ASC can, e.g., be used in the early detection or diagnosis of colorectal cancer.

9 Claims, 7 Drawing Sheets

SEQUENCE LISTING

<160> NUMBER OF SEQ ID NOS: 10

<210> SEQ ID NO 1
<211> LENGTH: 195
<212> TYPE: PRT
<213> ORGANISM: Homo sapiens

<400> SEQUENCE: 1

Met Gly Arg Ala Arg Asp Ala Ile Leu Asp Ala Leu Glu Asn Leu Thr
 1               5                  10                  15

Ala Glu Glu Leu Lys Lys Phe Lys Leu Lys Leu Leu Ser Val Pro Leu
            20                  25                  30

Arg Glu Gly Tyr Gly Arg Ile Pro Arg Gly Ala Leu Leu Ser Met Asp
        35                  40                  45

Ala Leu Asp Leu Thr Asp Lys Leu Val Ser Phe Tyr Leu Glu Thr Tyr
    50                  55                  60

Gly Ala Glu Leu Thr Ala Asn Val Leu Arg Asp Met Gly Leu Gln Glu
65                  70                  75                  80

Met Ala Gly Gln Leu Gln Ala Ala Thr His Gln Gly Ser Gly Ala Ala
                85                  90                  95

Pro Ala Gly Ile Gln Ala Pro Pro Gln Ser Ala Ala Lys Pro Gly Leu
            100                 105                 110

His Phe Ile Asp Gln His Arg Ala Ala Leu Ile Ala Arg Val Thr Asn
        115                 120                 125

Val Glu Trp Leu Leu Asp Ala Leu Tyr Gly Lys Val Leu Thr Asp Glu
    130                 135                 140

Gln Tyr Gln Ala Val Arg Ala Glu Pro Thr Asn Pro Ser Lys Met Arg
145                 150                 155                 160

Lys Leu Phe Ser Phe Thr Pro Ala Trp Asn Trp Thr Cys Lys Asp Leu
                165                 170                 175

Leu Leu Gln Ala Leu Arg Glu Ser Gln Ser Tyr Leu Val Glu Asp Leu
            180                 185                 190

Glu Arg Ser
        195

<210> SEQ ID NO 2
<211> LENGTH: 53
<212> TYPE: DNA
<213> ORGANISM: Artificial Sequence
<220> FEATURE:
<223> OTHER INFORMATION: Description of Artificial Sequence: Synthetic primer

<400> SEQUENCE: 2

```
atgcgaattc attaaagagg agaaattaac tatgaaagta gcaaaagacc tgg            53
```

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3

```
gcatgagctc acggccttca ataccgccac cagagccacc                           40
```

<210> SEQ ID NO 4
<211> LENGTH: 72
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4

```
atgcggatcc ggtggcggtt ccggcggtgg ctctggtggc ggtattgaag gccgtgggcg     60
cgcgcgcgac gc                                                         72
```

<210> SEQ ID NO 5
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5

```
gcataagctt tcattagtga tggtgatggt gatgggaacc gccaccgctc cgctccaggt     60
cctcc                                                                 65
```

<210> SEQ ID NO 6
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

```
Gly Gly Gly Ser Gly Gly Gly Ser Gly Gly Gly Ser Gly Gly Gly Ser
 1               5                  10                  15

Gly Gly Gly Ser Gly Gly Gly Ile Glu Gly Arg
            20                  25
```

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

```
Gly Gly Gly Ser His His His His His His
 1               5                  10
```

-continued

```
<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 8

His His His His His His
  1               5

<210> SEQ ID NO 9
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Gly Gly Ser Gly Gly Gly Ser Gly Gly Gly Ser Gly Gly Gly Ser
  1               5                  10                  15

Gly Gly Gly Ser Gly Gly Gly
             20

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ile Glu Gly Arg
  1
```

ASC AS A MARKER FOR COLORECTAL CANCER

RELATED APPLICATIONS

This application is a continuation of PCT/EP2005/013869 filed Dec. 22, 2005 and claims priority to EP 05008660.2 filed Apr. 20, 2005 and EP 04030619.3 filed Dec. 23, 2004.

FIELD OF THE INVENTION

The present invention relates to the diagnosis of colorectal cancer. It relates to the use of apoptosis-associated speck-like protein containing a caspase-associated recruitment domain (ASC) in the diagnosis of colorectal cancer. Furthermore, it especially relates to a method for diagnosis of colorectal cancer from a liquid sample derived from an individual by measuring ASC in said sample. Measurement of ASC can, e.g., be used in the early detection of colorectal cancer or in the surveillance of patients who undergo surgery.

BACKGROUND

Cancer remains a major public health challenge despite progress in detection and therapy. Among the various types of cancer, colorectal cancer (CRC) is one of the most frequent cancers in the Western world.

Colorectal cancer most frequently progresses from adenomas (polyps) to malignant carcinomas. The different stages of CRC used to be classified according to Dukes' stages A to D.

The staging of cancer is the classification of the disease in terms of extent, progression, and severity. It groups cancer patients so that generalizations can be made about prognosis and choice of therapy.

Today the TNM system is the most widely used classification of the anatomical extent of cancer. It represents an internationally accepted, uniform staging system. There are three basic variables: T (the extent of the primary tumor), N (the status of regional lymph nodes) and M (the presence or absence of distant metastases). The TNM criteria are published by the UICC (International Union Against Cancer), Edition 1997 (Sobin, L. H., and Fleming, I. D., TNM 80 (1997) 1803-4.

What is especially important is that early diagnosis of CRC translates to a much better prognosis. Malignant tumors of the colorectum arise from benign tumors, i.e. from adenoma. Therefore, best prognosis have those patients diagnosed at the adenoma stage. Patients diagnosed as early as in stage $T_{is}$, N0, M0 or T1-3; N0; M0, if treated properly have a more than 90% chance of survival 5 years after diagnosis as compared to a 5-year survival rate of only 10% for patients diagnosed when distant metastases are already present.

In the sense of the present invention early diagnosis of CRC refers to a diagnosis at a pre-malignant state (adenoma) or at a tumor stage where no metastases at all (neither proximal nor distal), i.e., adenoma, $T_{is}$, N0, M0 or TA-4; N0; M0 are present. $T_{is}$ denotes carcinoma in situ.

It is further preferred that CRC is diagnosed when a tumor has not yet fully grown through the bowel wall and thus neither the visceral peritoneum is perforated nor other organs or structures are invaded, i.e., that diagnosis is made at stage $T_{is}$, N0, M0 or T1-3; N0; M0 (T1-3; N0; M0).

The earlier cancer can be detected/diagnosed, the better is the overall survival rate. This is especially true for CRC. The prognosis in advanced stages of tumor is poor. More than one third of the patients will die from progressive disease within five years after diagnosis, corresponding to a survival rate of about 40% for five years. Current treatment is only curing a fraction of the patients and clearly has the best effect on those patients diagnosed in an early stage of disease.

With regard to CRC as a public health problem, it is essential that more effective screening and preventive measures for colorectal cancer be developed.

The earliest detection procedures available at present for colorectal cancer involve using tests for fecal blood or endoscopic procedures. However, significant tumor size must typically exist before fecal blood is detected. The sensitivity of the guaiac-based fecal occult blood tests is ~26%, which means 74% of patients with malignant lesions will remain undetected (Ahlquist, D. A., Gastroenterol. Clin. North Am. 26 (1997) 41-55). The visualization of precancerous and cancerous lesions represents the best approach to early detection, but colonoscopy is invasive with significant costs, risks, and complications (Silvis, S. E., et al., JAMA 235 (1976) 928-930; Geenen, J. E., et al., Am. J. Dig. Dis. 20 (1975) 231-235; Anderson, W. F., et al., J. Natl. Cancer Institute 94 (2002) 1126-1133).

In order to be of clinical utility, a new diagnostic marker as a single marker should be at least as good as the best single marker known in the art. Or a new marker should lead to a progress in diagnostic sensitivity and/or specificity either if used alone or in combination with one or more other markers, respectively. The diagnostic sensitivity and/or specificity of a test is best assessed by its receiver-operating characteristics, which will be described in detail below.

The clinical utility of biochemical markers in colorectal cancer has recently been reviewed by the European Group on Tumor Markers (EGTM) (Duffy, M. J., et al., Eur. J. Cancer 39 (2003) 718-727).

At present, primarily diagnostic blood tests based on the detection of carcinoembryonic antigen (CEA), a tumor-associated glycoprotein, are available to assist diagnosis in the field of CRC. CEA is increased in 95% of tissue samples obtained from patients with colorectal, gastric, and pancreatic cancers and in the majority of breast, lung, and head and neck carcinomas (Goldenberg, D. M., et al., J. Natl. Cancer Inst. (Bethesda) 57 (1976) 11-22). Elevated CEA levels have also been reported in patients with nonmalignant disease, and many patients with colorectal cancer have normal CEA levels in the serum, especially during the early stage of the disease (Carriquiry, L. A., and Pineyro, A., Dis. Colon Rectum 42 (1999) 921-929; Herrera, M. A., et al., Ann. Surg. 183 (1976) 5-9; Wanebo, H. J., et al., N. Engl. J. Med. 299 (1978) 448-451). The utility of CEA as measured from serum or plasma in detecting recurrences is reportedly controversial and has yet to be widely applied (Martell, R. E., et al., Int. J. Biol. Markers 13 (1998) 145-149; Moertel, C. G., et al., JAMA 270 (1993) 943-947).

In light of the available data, serum CEA determination possesses neither the sensitivity nor the specificity to enable its use as a screening test for colorectal cancer in the asymptomatic population (Reynoso, G., et al., JAMA 220 (1972) 361-365; Sturgeon, C., Clinical Chemistry 48 (2002) 1151-1159).

Whole blood, serum, or plasma are the most widely used sources of samples in clinical routine. The identification of an early CRC tumor marker that would aid in reliable cancer detection or provide early prognostic information could lead to a diagnostic assay that would greatly aid in the diagnosis and in the management of this disease. Therefore, an urgent clinical need exists to improve the in vitro assessment of CRC. It is especially important to improve the early diagnosis of CRC, since for patients diagnosed early on, chances of survival are much higher as compared to those diagnosed at a progressed stage of disease.

SUMMARY OF THE INVENTION

It was the task of the present invention to investigate whether a biochemical marker can be identified which may be used in assessing CRC.

Surprisingly, it has been found that use of the marker ASC can at least partially overcome the problems known from the state of the art.

The present invention therefore relates to a method for assessing colorectal cancer in vitro by biochemical markers comprising a) measuring in a sample the concentration of ASC, and b) using the concentration determined in step (a) in the assessment of colorectal cancer.

Another preferred embodiment of the invention is a method for assessing colorectal cancer comprising the steps of a) contacting a liquid sample obtained from an individual with a specific binding agent for ASC under conditions appropriate for formation of a complex between said binding agent and ASC, and b) correlating the amount of complex formed in (a) to the assessment of colorectal cancer.

Yet another preferred embodiment of the invention relates to a method for assessing colorectal cancer in vitro by biochemical markers, comprising measuring in a sample the concentration of ASC and of one or more other marker of colorectal cancer and using the concentrations determined in the assessment of colorectal cancer.

The present invention also relates to the use of a marker panel comprising at least ASC and CYFRA 21-1 in the assessment of CRC.

The present invention also relates to the use of a marker panel comprising at least ASC and NSE in the assessment of CRC.

The present invention also provides a kit for performing the method according to the present invention comprising at least the reagents required to specifically measure ASC and CYFRA 21-1, respectively, and optionally auxiliary reagents for performing the measurement.

The present invention also provides a kit for performing the method according to the present invention comprising at least the reagents required to specifically measure ASC and NSE, respectively, and optionally auxiliary reagents for performing the measurement.

In a further preferred embodiment the present invention relates to a method for assessing colorectal cancer in vitro comprising the steps of a) measuring in a sample the concentration of ASC, b) optionally measuring in the sample the concentration of one or more other marker of colorectal cancer, and c) using the concentrations determined in step (a) and optionally step (b) in the assessment of colorectal cancer.

DETAILED DESCRIPTION OF THE INVENTION

Figure 1:
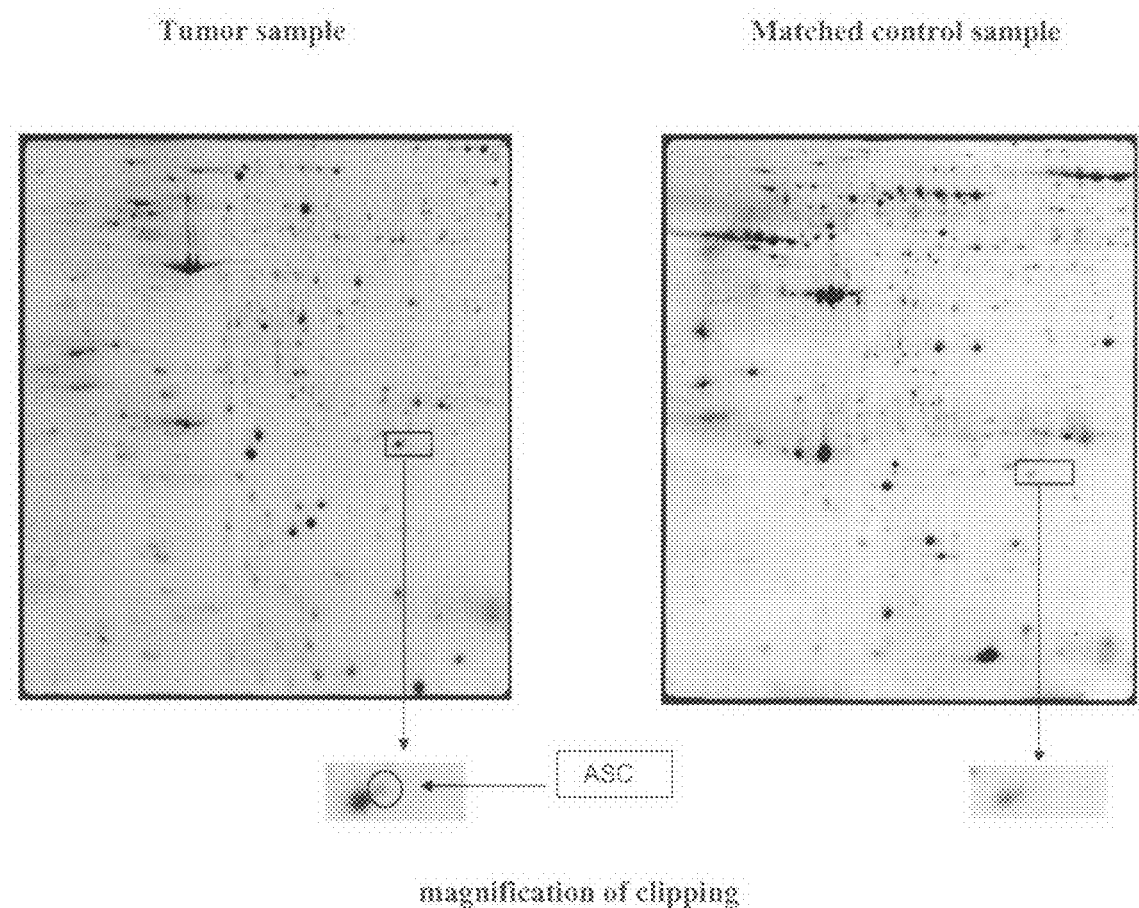
FIG. 1 The figure shows a 2-D gel, loaded with a breast tumor sample (left side) and a gel loaded with a matched control sample (right side). The circle in the enlarged section of these gels indicates the position for the protein ASC. Using the same method, this protein has not been detected in healthy tissue. ASC migrates in the 2-D gel corresponding to an isoelectric point of about pH 6 and an apparent molecular weight of about 22 kDa.

As used herein, each of the following terms have the meaning associated with it in this section:

The articles "a" and "an" are used herein to refer to one or to more than one (i.e. to at least one) of the grammatical object of the article. By way of example, "a marker" means one marker or more than one marker.

The term "marker" or "biochemical marker" as used herein refers to a molecule to be used as a target for analyzing patient test samples. Examples of such molecular targets are proteins or polypeptides themselves as well as antibodies present in a sample. Proteins or polypeptides used as a marker in the present invention are contemplated to include any variants of said protein as well as fragments of said protein or said variant, in particular, immunologically detectable fragments. One of skill in the art will recognize that proteins which are released by cells or present in the extracellular matrix which become damaged, e.g., during inflammation could become degraded or cleaved into such fragments. Certain markers are synthesized in an inactive form which may be subsequently activated by proteolysis. As the skilled artisan will appreciate, proteins or fragments thereof may also be present as part of a complex. Such complex also may be used as a marker in the sense of the present invention. Variants of a marker polypeptide are encoded by the same gene but differ in their PI or MW or both (e.g., as a result of alternative mRNA or pre-mRNA processing, e.g. alternative splicing or limited proteolysis) and in addition, or in the alternative, may arise from differential post-translational modification (e.g., glycosylation, acylation, and/or phosphorylation).

The term "assessing colorectal cancer" is used to indicate that the method according to the present invention will (alone or together with other markers or variables, e.g., the criteria set forth by the UICC (UICC (International Union Against Cancer), Sobin, L. H., Wittekind, Ch. (eds), TNM Classification of Malignant Tumours, fifth edition, 1997)) e.g., aid the physician in establishing or confirming the absence or presence of CRC or aid the physician in the prognosis, the detection of recurrence (follow-up of patients after surgery) and/or the monitoring of treatment, especially of chemotherapy.

The term "sample" as used herein refers to a biological sample obtained for the purpose of evaluation in vitro. In the methods of the present invention, the sample or patient sample preferably may comprise any body fluid. Preferred test samples include blood, serum, plasma, urine, saliva, and synovial fluid. Preferred samples are whole blood, serum, plasma, or synovial fluid, with plasma or serum being most preferred. As the skilled artisan will appreciate, any such assessment is made in vitro. The patient sample is discarded afterwards. The patient sample is solely used for the in vitro method of the invention, and the material of the patient sample is not transferred back into the patient's body. Typically, the sample is a liquid sample, e.g., whole blood, serum, or plasma.

In a preferred embodiment, the present invention relates to a method for assessing CRC in vitro by biochemical markers, comprising measuring in a sample the concentration of ASC and using the concentration determined in the assessment of CRC.

The "apoptosis-associated speck-like protein containing a caspase-associated recruitment domain" (ASC), also known as "target of methylation-induced silencing 1" (TMS1) (Swiss-PROT: Q9ULZ3) is characterized by the sequence given in SEQ ID NO: 1. This sequence translates to a theoretical molecular weight of 21,627 Da and to a theoretical isoelectric point of pH 6.29.

Caspase-associated recruitment domains (CARDs) mediate the interaction between adaptor proteins such as APAF1 (apoptotic protease activating factor 1) and the pro-form of caspases (e.g., CASP 9) participating in apoptosis. ASC is a member of the CARD-containing adaptor protein family.

By immunoscreening a promyelocytic cell line, Masumoto et al. isolated a cDNA encoding ASC. The deduced 195-amino acid protein contains an N-terminal pyrin-like domain (PYD) and an 87-residue C-terminal CARD. Western blot analysis showed expression of a 22-kDa protein and indicated that ASC may have proapoptotic activity by increasing the susceptibility of leukemia cell lines to apoptotic stimuli by anticancer drugs (Masumoto, J., et al., J. Biol. Chem. 274 (1999) 33835-33838).

Methylation-sensitive restriction PCR and methylation-specific PCR (MSP) analyses by Conway et al. indicated that silencing of ASC correlates with hypermethylation of the CpG island surrounding exon1 and that overexpression of DNMT1 (DNA cytosine-5-methyltransferase-1) promotes hypermethylation and silencing of ASC. Breast cancer cell lines, but not normal breast tissue, exhibited complete methylation of ASC and expressed no ASC message. Expression of ASC in breast cancer cell lines inhibited growth and reduced the number of surviving colonies. Conway et al. concluded that ASC functions in the promotion of caspase-dependent apoptosis and that overexpression of ASC inhibits the growth of breast cancer cells (Conway, K. E., et al., Cancer Research 60 (2000) 6236-6242).

McConnell and Vertino showed that inducible expression of ASC inhibits cellular proliferation and induces DNA fragmentation that can be blocked by caspase inhibitor. Immunofluorescence microscopy demonstrated that induction of apoptosis causes a CARD-dependent shift from diffuse cytoplasmic expression to spherical perinuclear aggregates (Mc-Connell, B. B., and Vertino, P. M., Cancer Research 60 (2000) 6243-6247).

Moriani et al. observed methylation of ASC gene not only in breast cancer cells but also in gastric cancer. They suggested a direct role for aberrant methylation of the ASC gene in the progression of breast and gastric cancer involving down-regulation of the proapoptotic ASC gene (Moriani, R., et al., Anticancer Research 22 (2002) 4163-4168).

Conway et al. examined primary breast tissues for TMS1 methylation and compared the results to methylation in healthy tissues (Conway K. E., et al., Cancer Research 60 (2000) 6236-6242). Levine et al. found that ASC silencing was not correlated with methylation of specific CpG sites, but rather was associated with dense methylation of ASC CpG island. Breast tumor cell lines containing exclusively methylated ASC copies do not express ASC, while in partially methylated cell lines the levels of ASC expression are directly related to the percentage of methylated ASC alleles present in the cell population (Levine, J. J., et al., Oncogene 22 (2003) 3475-3488).

Virmani et al. examined the methylation status of ASC in lung cancer and breast cancer tissue. They found that aberrant methylation of ASC was present in 46% of breast cancer cell lines and in 32% of breast tumor tissue. Methylation was rare in non-malignant breast tissue (7%) (Virmani, A., et al., Int. J. Cancer 106 (2003) 198-204).

Shiohara et al. found out that up-regulation of ASC is closely associated with inflammation and apoptosis in human neutrophils (Shiohara, M., et al., Blood 98 (2001) 229a).

Masumoto et al. observed high levels of ASC abundantly expressed in epithelial cells and leucocytes (Masumoto, J., et al., Journal Histochem. Cytochem. 49 (2001) 1269-1275).

As obvious to the skilled artisan, the present invention shall not be construed to be limited to the full-length protein ASC of SEQ ID NO: 1. Physiological or artificial fragments of ASC, secondary modifications of ASC, as well as allelic variants of ASC are also encompassed by the present invention. Artificial fragments preferably encompass a peptide produced synthetically or by recombinant techniques, which at least comprises one epitope of diagnostic interest consisting of at least 6 contiguous amino acids as derived from the sequence disclosed in SEQ ID NO: 1. Such fragment may advantageously be used for generation of antibodies or as a standard in an immunoassay. More preferred the artificial fragment comprises at least two epitopes of interest appropriate for setting up a sandwich immunoassay.

The assessment method according to the present invention is based on a liquid sample which is derived from an individual. Unlike methods known in the art, ASC is specifically measured from this liquid sample by use of a specific binding agent.

A specific binding agent is, e.g., a receptor for ASC, a lectin binding to ASC or an antibody to ASC. A specific binding agent has at least an affinity of $10^7$ l/mol for its corresponding target molecule. The specific binding agent preferably has an affinity of 108 l/mol or even more preferred of 109 l/mol for its target molecule. As the skilled artisan will appreciate the term specific is used to indicate that other biomolecules present in the sample do not significantly bind to the binding agent specific for ASC. Preferably, the level of binding to a biomolecule other than the target molecule results in a binding affinity which is only 10%, more preferably only 5%, of the affinity of the target molecule or less. A most preferred specific binding agent will fulfill both the above minimum criteria for affinity as well as for specificity.

A specific binding agent preferably is an antibody reactive with ASC. The term antibody refers to a polyclonal antibody, a monoclonal antibody, fragments of such antibodies, as well as to genetic constructs comprising the binding domain of an antibody.

Any antibody fragment retaining the above criteria of a specific binding agent can be used. Antibodies are generated by state of the art procedures, e.g., as described in Tijssen (Tijssen, P., Practice and Theory of Enzyme Immunoassays 11 (1990,) the whole book, especially pages 43-78; Elsevier, Amsterdam). In addition, the skilled artisan is well aware of methods based on immunosorbents that can be used for the specific isolation of antibodies. By these means the quality of polyclonal antibodies and hence their performance in immunoassays can be enhanced. (Tijssen, P., supra, pages 108-115).

For the achievements as disclosed in the present invention, polyclonal antibodies raised in rabbits have been used. However, clearly also polyclonal antibodies from different species, e.g. rats or guinea pigs, as well as monoclonal antibodies can also be used. Since monoclonal antibodies can be produced in any amount required with constant properties, they represent ideal tools in development of an assay for clinical routine. The generation and use of monoclonal antibodies to ASC in a method according to the present invention is yet another preferred embodiment.

As the skilled artisan will appreciate now that ASC has been identified as a marker which is useful in the diagnosis of CRC, alternative ways may be used to reach a result comparable to the achievements of the present invention. For example, alternative strategies to generate antibodies may be used. Such strategies comprise among others the use of synthetic peptides representing an epitope of ASC for immunization. Alternatively, DNA immunization also known as DNA vaccination, may be used.

For measurement the liquid sample obtained from an individual is incubated with the specific binding agent for ASC under conditions appropriate for formation of a binding agent-ASC complex. Such conditions need not be specified since the skilled artisan without any inventive effort can easily identify such appropriate incubation conditions.

As a final step according to the method disclosed in the present invention, the amount of complex is measured and correlated to the diagnosis of CRC. As the skilled artisan will appreciate there are numerous methods to measure the amount of the specific binding agent-ASC complex all described in detail in relevant textbooks (cf., e.g., Tijssen P., supra, or Diamandis, et al., eds. (1996) Immunoassay, Academic Press, Boston).

Preferably ASC is detected in a sandwich type assay format. In such assay a first specific binding agent is used to capture ASC on the one side and a second specific binding agent, which is labeled to be directly or indirectly detectable is used on the other side.

As mentioned above, it has surprisingly been found that ASC can be measured from a liquid sample obtained from an individual sample. No tissue and no biopsy sample is required to apply the marker ASC in the assessment of CRC.

In a preferred embodiment the method according to the present invention is practiced with serum as liquid sample material. In a further preferred embodiment the method according to the present invention is practiced with plasma as liquid sample material. In a further preferred embodiment the method according to the present invention is practiced with whole blood as liquid sample material.

Furthermore stool can be prepared in various ways known to the skilled artisan to result in a liquid sample as well. Such sample liquid derived from stool also represents a preferred embodiment according to the present invention.

The inventors of the present invention have surprisingly been able to detect protein ASC in a bodily fluid sample. Even more surprising they have been able to demonstrate that the presence of ASC in such liquid sample obtained from an individual can be correlated to the assessment of colorectal cancer. Preferably, an antibody to ASC is used in a qualitative (ASC present or absent) or quantitative (ASC amount is determined) immunoassay.

Measuring the level of protein ASC has proven very advantageous in the field of CRC. Therefore, in a further preferred embodiment, the present invention relates to use of protein ASC as a marker molecule in the assessment of colorectal cancer from a liquid sample obtained from an individual.

The ideal scenario for diagnosis would be a situation wherein a single event or process would cause the respective disease as, e.g., in infectious diseases. In all other cases correct diagnosis can be very difficult, especially when the etiology of the disease is not fully understood as is the case of CRC. As the skilled artisan will appreciate, no biochemical marker, for example in the field of CRC, is diagnostic with 100% specificity and at the same time 100% sensitivity for a given disease. Rather, biochemical markers are used to assess with a certain likelihood or predictive value the presence or absence of a disease. Therefore, in routine clinical diagnosis various clinical symptoms and biological markers are generally considered together in the diagnosis, treatment, and management of the underlying disease.

Biochemical markers can either be determined individually or, in a preferred embodiment of the invention, they can be measured simultaneously using a chip- or a bead-based array technology. The concentrations of the biomarkers are then interpreted independently using an individual cut-off for each marker or they are combined for interpretation.

In a further preferred embodiment of the invention the assessment of colorectal cancer according to the present invention is performed in a method comprising the steps of a) measuring in a sample the concentration of ASC, b) optionally measuring in the sample one or more other markers of colorectal cancer, and c) using the concentration determined in step (a) and optionally the concentration(s) determined in step (b) in the assessment of colorectal cancer.

Preferably the method for assessment of CRC is performed by measuring the concentration of ASC and of one or more other markers and by using the concentration of ASC and the concentration(s) of the one or more other markers in the assessment of CRC.

The present invention is also directed to a method for assessing CRC in vitro by biochemical markers comprising measuring in a sample the concentration of ASC and of one or more other markers of CRC and using the concentrations determined in the assessment of CRC.

According to the data shown in the examples section, the marker ASC in the univariate analysis has (at a specificity of about 90%) a sensitivity for CRC of 54.7%. In the assessment of CRC the marker ASC will be of advantage in one or more of the following aspects: screening, diagnostic aid, prognosis, monitoring of chemotherapy, and follow-up.

Screening

CRC is the second most common malignancy of both males and females in developed countries. Because of its high prevalence, its long asymptomatic phase and the presence of premalignant lesions, CRC meets many of the criteria for screening. Clearly, a serum tumor marker which has acceptable sensitivity and specificity would be more suitable for screening than either FOB testing or endoscopy.

As the data given in the examples section demonstrate, ASC alone will not suffice to allow for a general screening, e.g. of the at risk population, for CRC. Most likely no single biochemical marker in the circulation will ever meet the sensitivity and specificity criteria required for screening purposes. Rather it has to be expected that a marker panel will have to be used in CRC screening. The data established in the present invention indicate that the marker ASC will form an integral part of a marker panel appropriate for screening purposes. The present invention therefore relates to the use of ASC as one marker of a CRC marker panel for CRC screening purposes. The present data further indicate that certain combinations of markers will be advantageous in the screening for CRC. Therefore the present invention also relates to the use of a marker panel comprising ASC and CYFRA 21-1, or of a marker panel comprising ASC and NSE, or of a marker panel comprising ASC and CYFRA 21-1 and NSE for the purpose of screening for CRC.

Diagnostic Aid

Preoperative CEA values are of limited diagnostic value. Nonetheless the European Committee on Tumor Markers (ECTM) recommends that CFA should be measured before surgery in order to establish a baseline value and for assessing the prognosis. Since ASC as a single marker according to the data of the present invention might be at least as good a single marker as CEA or even superior it has to be expected that ASC will be used as a diagnostic aid, especially by establishing a baseline value before surgery.

The present invention thus also relates to the use of ASC for establishing a baseline value before surgery for CRC.

Prognosis

The gold standard for determining prognosis in patients with CRC is the extent of disease as defined by the Dukes, TNM or other staging systems. If a marker such as CEA is to be used for predicting outcome, it must: provide stronger prognostic information than that offered by existing staging systems, provide information independent of the existing systems, or provide prognostic data within specific subgroups defined by existing criteria, e.g. in Dukes B or node-negative patients.

Recently, an American Joint Committee on Cancer (AJCC) Consensus Conference suggested that CEA should be added to the TNM staging system for colorectal cancer. The CEA level should be designated as follows: CX, CEA cannot be assessed; CO, CEA not elevated (<5 µg/l) or CEA1, CEA elevated (>5 µg/l) (Compton, C., et al., Cancer 88 (2000) 1739-1757).

As ASC alone significantly contributes to the differentiation of CRC patients from healthy controls or from healthy controls plus non-malignant colon diseases, it has to be expected that it will aid in assessing the prognosis of patients suffering from CRC. The level of preoperative ASC will most likely be combined with one or more other markers for CRC and/or the TNM staging system, as recommended for CEA by the AJCC. In a preferred embodiment ASC is used in the prognosis of patients with CRC.

Monitoring of Chemotherapy

A number of reports have described the use of CEA in monitoring the treatment of patients with advanced CRC (for review, see Refs. Duffy, M. J., Clin. Chem. 47 (2001) 625-630; Fletcher, R. H., Ann. Int. Med. 104 (1986) 66-73; Anonymous, J. Clin. Oncol. 14 (1996) 2843-2877). Most of these were retrospective, non-randomized and contained small numbers of patients. These studies suggested (a) that patients with a decrease in CEA levels while receiving chemotherapy generally had a better outcome than those patients whose CEA levels failed to decrease and (b) for almost all patients, increases in CEA levels were associated with disease progression.

Due to the data shown in the example section, it has to be expected that ASC will be at least as good a marker for monitoring of chemotherapy as CEA. The present invention therefore also relates to the use of ASC in the monitoring of CRC patients under chemotherapy.

Follow-Up

Approximately 50% of patients who undergo surgical resection aimed at cure, later develop recurrent of metastatic disease (Berman, J. M., et al., Lancet 355 (2000) 395-399). Most of these relapses occur within the first 2-3 years of diagnosis and are usually confined to the liver, lungs or locoregional areas. Since recurrent/metastatic disease is invariably fatal, considerable research has focused on its identification at an early and thus potentially treatable stage. Consequently, many of these patients undergo a postoperative surveillance program which frequently includes regular monitoring with CEA.

Serial monitoring with CEA has been shown to detect recurrent/metastatic disease with a sensitivity of approximately of 80%, specificity of approximately 70% and provides an average lead-time of 5 months (for review, see Duffy, M. J., et al., supra, and Fletcher, R. H., supra). Furthermore, CEA was the most frequent indicator of recurrence in asymptomatic patients (Pietra, N., et al., Dis. Colon Rectum 41 (1998) 1127-1133 and Graham, R. A., et al., Ann. Surg. 228 (1998) 59-63) and was more cost-effective than radiology for the detection of potentially curable recurrent disease. As regards sites of recurrence/metastasis, CEA was most sensitive (almost 100%) for the detection of liver metastasis. On the other hand, CEA was less reliable for diagnosing locoregional recurrences, the sensitivity being only approximately 60% (Moertel, C. G., et al., Jama 270 (1993)943-7)

As a compromise between patient convenience, costs and efficiency of disease detection, the EGTM Panel like the ASCO Panel (Anonymous, J. Clin. Oncol. 14 (1996) 2843-2877) suggests that CEA testing be carried out every 2-3 months for at least 3 years after the initial diagnosis. After 3 years, testing could be carried out less frequently, e.g. every 6 months. No evidence exists, however, to support this frequency of testing.

As the above discussion of the state of the art shows, that the follow-up of patients with CRC after surgery is one of the most important fields of use for an appropriate biochemical marker. Due to the high sensitivity of ASC in the CRC patients investigated it is expected that ASC alone or in combination with one or more other marker will be of great help in the follow-up of CRC patients, especially in CRC patients after surgery. The use of a marker panel comprising ASC and one or more other marker of CRC in the follow-up of CRC patients represents a further preferred embodiment of the present invention.

The present invention discloses and therefore in a preferred embodiment relates to the use of ASC in the diagnostic field of CRC or in the assessment of CRC, respectively.

In yet a further preferred embodiment the present invention relates to the use of ASC as a marker molecule for colorectal cancer in combination with one or more marker molecules for colorectal cancer in the assessment of colorectal cancer from a liquid sample obtained from an individual. In this regard, the expression "one or more" denotes 1 to 20, preferably 1 to 10, preferably 1 to 5, more preferred 3 or 4. ASC and the one or more other marker form a CRC marker panel.

Thus, a preferred embodiment of the present invention is the use of ASC as a marker molecule for colorectal cancer in combination with one or more marker molecules for colorectal cancer in the assessment of colorectal cancer from a liquid sample obtained from an individual. Preferred selected other CRC markers with which the measurement of ASC may be combined are NSE, CYFRA 21-1, NMMT, CA 19-9, CA 72-4, and/or CEA. Yet further preferred the marker panel used in the assessment of CRC comprises ASC and at least one other marker molecule selected from the group consisting of NSE, CYFRA 21-1 and NMMT.

The markers which preferably are combined with ASC or which form part of the CRC marker panel comprising ASC, respectively, are discussed in more detail below.

NSE (Neuron-Specific Enolase)

The glycolytic enzyme enolase (2-phospho-D-glycerate hydrolase, EC 4.2.1.11, molecular weight approx. 80 kD) occurs in a variety of dimeric isoforms comprising three immunologically different subunits termed α, β, and γ. The α-subunit of enolase occurs in numerous types of tissue in mammals, whereas the β-subunits found mainly in the heart and in striated musculature. The enolase isoforms αγ and γγ, which are referred to as neuron-specific enolase (NSE) or γ-enolase, are primarily detectable in high concentrations in neurons and neuro-endocrine cells as well as in tumors originating from them. (Lamerz R., NSE (Neuronen-spezifische Enolase), γ-Enolase. In: Thomas L (ed) Clinical Laboratory Diagnosis, TH-Books, Frankfurt, $1^{st}$ English Edition 1998: 979-981, 5. deutsche Auflage 1998:1000-1003)

NSE is described as the marker of first choice in the monitoring of small cell bronchial carcinoma, (Lamerz R., supra), whereas CYFRA 21-1 is superior to NSE for non-small cell bronchial carcinoma. (Ebert W., et al., Eur. J. Clin. Chem. Clin. Biochem 32 (1994) 189-199).

Elevated NSE concentrations are found in 60-81% of cases of small cell bronchial carcinoma.

For NSE there is no correlation to the site of metastasis or to cerebral metastasis, but there is good correlation to the clinical stage, i.e. the extent of the disease.

In response to chemotherapy there is a temporary rise in the NSE level 24-72 hours after the first therapy cycle as a result of cytolysis of the tumor cells. This is followed within a week or by the end of the first therapy cycle by a rapid fall in the serum values (which were elevated prior to therapy). By contrast, non-responders to therapy display levels which are constantly elevated or fail to fall into the reference range. During remission, 80-96% of the patients have normal values. Rising NSE values are found in cases of relapse. The rise occurs in some cases with a latent period of 1-4 months, is often exponential (with a doubling time of 10-94 days) and correlates with the survival period. NSE is useful as a single prognostic factor and activity marker during the monitoring of therapy and the course of the disease in small cell bronchial carcinoma: diagnostic sensitivity 93%, positive predictive value 92% (Lamerz R., supra)

In neuroblastoma NSE serum values above 30 ng/ml are found in 62% of the affected children. The medians rise in accordance with the stage of the disease. There is a significant correlation between the magnitude or frequency of pathological NSE values and the stage of disease; there is an inverse correlation with illness-free survival.

68-73% of the patients with seminoma have a clinically significant NSE elevation. (Lamerz R., supra). There is a utilizable correlation with the clinical course of the disease.

NSE has also been measured in other tumors: Non-pulmonary malignant diseases show values above 25 ng/ml in 22% of the cases (carcinomas in all stages). Brain tumors such as glioma, meningioma, neurofibroma, and neurinoma are only occasionally accompanied by elevated serum NSE values. In primary brain tumors or brain metastasis and in malignant melanoma and pheochromocytoma, elevated NSE-values can occur in the CSF (cerebrospinal fluid). Increased NSE concentrations have been reported for 14% of organ-restricted and 46% of metastasizing renal carcinomas, with a correlation to the grade as an independent prognosis factor.

In benign disease elevated serum NSE concentrations (>12 ng/ml) have been found in patients with benign pulmonary diseases and cerebral diseases. Elevated values, mainly in the liquor, have been found in cerebrovascular meningitis, disseminated encephalitis, spinocerebellar degeneration, cerebral ischemia, cerebral infarction, intracerebral hematoma, subarachnoid hemorrhage, head injuries, inflammatory brain diseases, organic epilepsy, schizophrenia, and Jakob-Creutzfeld disease. (Lamerz R., supra)

NSE has been measured on an ELECSYS analyzer (Roche Diagnostics GmbH) using Roche product number 12133113 according to the manufacturers instructions.

CA 19-9 (Carbohydrate Antigen 19-9)

The CA 19-9 values measured are defined by the use of the monoclonal antibody 1116-NS-19-9. The 1116-NS-19-9-reactive determinants on a glycolipid having a molecular weight of approx. 10,000 daltons are measured. This mucin corresponds to a hapten of Lewis-a blood group determinants and is a component of a number of mucous membrane cells. (Koprowski, H., et al., Somatic Cell Genet. 5 (1979) 957-971).

3-7% of the population have the Lewis a-negative/b-negative blood group configuration and are unable to express the mucin with the reactive determinant CA 19-9. This must be taken into account when interpreting the findings.

Mucin occurs in fetal gastric, intestinal and pancreatic epithelia. Low concentrations can also be found in adult tissue in the liver, lungs, and pancreas (Stieber, P. and Fateh-Moghadam, A., Boeringer Mannheim, Cat. No. 1536869 (engl), 1320947 (dtsch). ISBN 3-926725-07-9 dtsch/engl., Juergen Hartmann Verlag, Marloffstein-Rathsberg (1993); Herlyn, M., et al., J. Clin. Immunol 2 (1982) 135-140).

CA 19-9 assay values can assist in the differential diagnosis and monitoring of patients with pancreatic carcinoma (sensitivity 70-87%) (Ritts, R. E., Jr., et al., Int. J. Cancer 33 (1984) 339-345). There is no correlation between tumor mass and the CA 19-9 assay values. However, patients with CA 19-9 serum levels above 10,000 U/mL almost always have distal metastasis.

The determination of CA 19-9 cannot be used for the early detection of pancreatic carcinoma (Steinberg, W. M., et al., Gastroenterology 90 (1986) 343-349).

In hepatobiliary carcinoma the CA 19-9 values provide a sensitivity of 50-75%. The concomitant determination of CA 72-4 and CEA is recommended in case of gastric carcinoma.

In colorectal carcinoma, determination of CEA alone is adequate; only in rare CEA-negative cases the determination of CA 19-9 can be useful.

As the mucin is excreted exclusively via the liver, even slight cholestasis can lead to clearly elevated CA 19-9 serum levels in some cases. Elevated CA 19-9 values are also found with a number of benign and inflammatory diseases of the gastrointestinal tract and the liver, as well as in cystic fibrosis.

CA 19-9 has been measured on an ELECSYS analyzer using Roche product number 11776193 according to the manufacturers instructions.

CEA Carcinoembryonic Antigen

CEA is a monomeric glycoprotein (molecular weight approx. 180.000 dalton) with a variable carbohydrate component of approx. 45-60% (Gold, P. and Freedman, S. O., J. Exp Med 121 (1965) 439-462).

CEA, like AFP, belongs to the group of carcinofetal antigens that are produced during the embryonic and fetal period. The CEA gene family consists of about 17 active genes in two subgroups. The first group contains CEA and the Non-specific Cross-reacting Antigens (NCA); the second group contains the Pregnancy-Specific Glycoproteins (PSG).

CEA is mainly found in the fetal gastrointestinal tract and in fetal serum. It also occurs in slight quantities in intestinal, pancreatic, and hepatic tissue of healthy adults. The formation of CEA is repressed after birth, and accordingly serum CEA values are hardly measurable in healthy adults.

High CEA concentrations are frequently found in cases of colorectal adenocarcinoma (Stieber, P. and Fateh-Moghadam, A., supra). Slight to moderate CEA elevations (rarely >10 ng/mL) occur in 20-50% of benign diseases of the intestine, the pancreas, the liver, and the lungs (e.g. liver cirrhosis, chronic hepatitis, pancreatitis, ulcerative colitis, Crohn's Disease, emphysema) (Stieber, P. and Fateh-Moghadam, A., supra). Smokers also have elevated CEA values.

The main indication for CEA determinations is the follow-up and therapy management of colorectal carcinoma.

CEA determinations are not recommended for cancer-screening in the general population. CEA concentrations within the normal range do not exclude the possible presence of a malignant disease.

The antibodies in assay manufactured by Roche Diagnostics react with CEA and (as with almost all CEA methods) with the meconium antigen (NCA2). Cross-reactivity with NCA1 is 0.7% (Hammarstrom, S., et al., Cancer Res. 49 (1989) 48524858 and Bormer, O. P., Tumor Biol. 12 (1991) 9-15)

CEA has been measured on an ELECSYS analyzer using Roche product number 11731629 according to the manufacturers instructions.

CYFRA 21-1

An assay for CYFRA 21-1 specifically measures a soluble fragment of cytokeratin 19 as present in the circulation. The measurement of CYFRA 21-1 is typically based upon two monoclonal antibodies (Bodenmueller, H., et al., Int. J. Biol. Markers 9 (1994) 75-81). In the CYFRA 21-1 assay from Roche Diagnostics, Germany, the two specific monoclonal antibodies (KS 19.1 and BM 19.21) are used and a soluble fragment of cytokeratin 19 having a molecular weight of approx. 30,000 daltons is measured.

Cytokeratins are structural proteins forming the subunits of epithelial intermediary filaments. Twenty different cytokeratin polypeptides have so far been identified. Due to their specific distribution patterns they are eminently suitable for use as differentiation markers in tumor pathology. Intact cytokeratin polypeptides are poorly soluble, but soluble fragments can be detected in serum. (Bodenmueller, H., et al., supra).

CYFRA 21-1 is a well-established marker for non-small-cell lung carcinoma (NSCLC). The main indication for CYFRA 21-1 is monitoring the course of non-small cell lung cancer (NSCLC). (Sturgeon, C., Clinical Chemistry 48 (2002) 1151-1159).

High CYFRA 21-1 serum levels indicate an advanced tumor stage and a poor prognosis in patients with non-small-cell lung cancer. (van der Gaast, A., et al., Br. J. Cancer 69 (1994) 525-528). A normal or only slightly elevated value does not rule out the presence of a tumor.

Successful therapy is documented by a rapid fall in the CYFRA 21-1 serum level into the normal range. A constant CYFRA 21-1 value or a slight or only slow decrease in the CYFRA 21-1 value indicates incomplete removal of a tumor or the presence of multiple tumors with corresponding therapeutic and prognostic consequences. Progression of the disease is often shown earlier by increasing CYFRA 21-1 values than by clinical symptomotology and imaging procedures.

It is accepted that in the primary diagnosis of pulmonary carcinoma should be made on the basis of clinical symptomotology, imaging or endoscopic procedures and intraoperative findings. An unclear circular focus in the lung together with CYFRA 21-1 values>30 ng/mL indicates with high probability the existence of primary bronchial carcinoma.

CYFRA 21-1 is also suitable for course-monitoring in myoinvasive cancer of the bladder. Good specificity is shown by CYFRA 21-1 relative to benign lung diseases (pneumonia, sarcoidosis, tuberculosis, chronic bronchitis, bronchial asthma, emphysema).

Slightly elevated values (up to 10 ng/mL) are rarely found in marked benign liver diseases and renal failure. There is no correlation with sex, age or smoking. The values for CYFRA 21-1 are also unaffected by pregnancy.

Recently it has been found that CYFRA 21-1 also is of use in detecting disease relapse and assessing treatment efficacy in the field of breast cancer (Nakata, B., et al., British J. of Cancer (2004) 1-6).

CYFRA 21-1 has been measured on an ELECSYS analyzer using Roche product number 11820966 according to the manufacturers instructions.

As mentioned further above CYFRA 21-1 is an established marker in the field of NSCLC. When developing and establishing CYFRA 21-1 for NSCLC, non-malignant disease controls derived from patients with certain lung non-malignant diseases have been used. This has been considered important to differentiate benign from malign lung diseases (H. Bodenmüller, et al., supra).

Since only recently it is possible to detect the marker CYFRA 21-1 in a significant percentage of samples derived from patients with CRC. In addition, the presence of CYFRA 21-1 in such liquid sample obtained from an individual can be used in the assessment of colorectal cancer. Particularly in combination with other markers CYFRA 21-1 is considered to be a very useful marker in the field of CRC.

NNMT

The protein nicotinamide N-methyltransferase (NNMT; Swiss-PROT: P40261) has an apparent molecular weight of 29.6 kDa and an isoelectric point of 5.56.

NNMT catalyzes the N-methylation of nicotinamide and other pyridines. This activity is important for biotransformation of many drugs and xenobiotic compounds. The protein has been reported to be predominantly expressed in liver and is located in the cytoplasm. NNMT has been cloned from cDNA from human liver and contained a 792-nucleotide open reading frame that encoded a 264-amino acid protein with a calculated molecular mass of 29.6 kDa. (Aksoy, S., et al., J. Biol. Chem. 269 (1994) 14835-14840). Little is known in the literature about a potential role of the enzyme in human cancer. In one paper, increased hepatic NNMT enzymatic activity was reported as a marker for cancer cachexia in mice (Okamura, A., et al., Jpn. J. Cancer Res. 89 (1998) 649-656). In a recent report, down-regulation of the NNMT gene in response to radiation in radiation sensitive cell lines was demonstrated (Kassem, H., et al., Int. J. Cancer 101 (2002) 454-460).

It has recently been found (WO 2004/057336) that NNMT will be of interest in the assessment of CRC. The immunoassay described in WO 2004/057336 has been used to measure the samples (CRC, healthy controls and non-malignant colon diseases) of the present study.

As the skilled artisan will appreciate there are many ways to use the measurements of two or more markers in order to improve the diagnostic question under investigation. In a quite simple, but nonetheless often effective approach, a positive result is assumed if a sample is positive for at least one of the markers investigated. This may e.g. the case when diagnosing an infectious disease, like AIDS.

Frequently, however, the combination of markers is evaluated. Preferably the values measured for markers of a marker panel, e.g. for ASC, CYFRA 21-1 and NSE, are mathematically combined and the combined value is correlated to the underlying diagnostic question. Marker values may be combined by any appropriate state of the art mathematical method. Well-known mathematical methods for correlating a marker combination to a disease employ methods like, discriminant analysis (DA) (i.e. linear-, quadratic-, regularized-DA), Kernel Methods (i.e. SVM), Nonparametric Methods (i.e. k-Nearest-Neighbor Classifiers), PLS (Partial Least Squares), Tree-Based Methods (i.e. Logic Regression, CART, Random Forest Methods, Boosting/Bagging Methods), Generalized Linear Models (i.e. Logistic Regression), Principal Components based Methods (i.e. SIMCA), Generalized Additive Models, Fuzzy Logic based Methods, Neural Networks and Genetic Algorithms based Methods. The skilled artisan will have no problem in selecting an appropriate method to evaluate a marker combination of the present invention. Preferably the method used in correlating the marker combination of the invention e.g. to the absence or presence of CRC is selected from DA (i.e. Linear-, Quadratic-, Regularized Discriminant Analysis), Kernel Methods (i.e. SVM), Nonparametric Methods (i.e. k-Nearest-Neighbor Classifiers), PLS (Partial Least Squares), Tree-Based Methods (i.e. Logic Regression, CART, Random Forest Methods, Boosting Methods), or Generalized Linear Models (i.e. Logistic Regression). Details relating to these statistical methods are found in the following references: Ruczinski, I., et al, J. of Computational and Graphical Statistics, 12 (2003) 475-511; Friedman, J. H., J. of the American Statistical Association 84 (1989) 165-175; Hastie, Trevor, Tibshirani, Robert, Friedman, Jerome, The Elements of Statistical Learning, Springer Series in Statistics, 2001; Breiman, L., Friedman, J. H., Olshen, R. A., Stone, C. J. (1984) Classification and regression trees, California: Wadsworth; Breiman, L., Random Forests, Machine Learning 45 (2001) 5-32; Pepe, M. S., The Statistical Evaluation of Medical Tests for Classification and Prediction, Oxford Statistical Science Series, 28 (2003); and Duda, R. O., Hart, P. E., Stork, D. G., Pattern Classification, Wiley Interscience, 2nd Edition (2001).

It is a preferred embodiment of the invention to use an optimized multivariate cut-off for the underlying combination of biological markers and to discriminate state A from state B, e.g. diseased from healthy. In this type of analysis the markers are no longer independent but form a marker panel. It could be established that combining the measurements of ASC, NSE and CYFRA 21-1, does particularly improve the diagnostic accuracy for CRC as compared to either healthy controls or, as also assessed, as compared to healthy controls plus non-malignant disease controls. Especially the later finding is of great importance, because a patient with a non-malignant disease may require quite a different treatment as a patient with CRC.

Accuracy of a test is best described by its receiver-operating characteristics (ROC) (see especially Zweig, M. H., and Campbell, G., Clin. Chem. 39 (1993) 561-577). The ROC graph is a plot of all of the sensitivity/specificity pairs resulting from continuously varying the decision thresh-hold over the entire range of data observed.

The clinical performance of a laboratory test depends on its diagnostic accuracy, or the ability to correctly classify subjects into clinically relevant subgroups. Diagnostic accuracy measures the test's ability to correctly distinguish two different conditions of the subjects investigated. Such conditions are for example health and disease or benign versus malignant disease.

In each case, the ROC plot depicts the overlap between the two distributions by plotting the sensitivity versus 1−specificity for the complete range of decision thresholds. On the y-axis is sensitivity, or the true-positive fraction [defined as (number of true-positive test results)/(number of true-positive+number of false-negative test results)]. This has also been referred to as positivity in the presence of a disease or condition. It is calculated solely from the affected subgroup. On the x-axis is the false-positive fraction, or 1−specificity [defined as (number of false-positive results)/(number of true-negative+number of false-positive results)]. It is an index of specificity and is calculated entirely from the unaffected subgroup. Because the true- and false-positive fractions are calculated entirely separately, by using the test results from two different subgroups, the ROC plot is independent of the prevalence of disease in the sample. Each point on the ROC plot represents a sensitivity/1-specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45° diagonal line from the lower left corner to the upper right corner. Most plots fall in between these two extremes. (If the ROC plot falls completely below the 45° diagonal, this is easily remedied by reversing the criterion for "positivity" from "greater than" to "less than" or vice versa.) Qualitatively, the closer the plot is to the upper left corner, the higher the overall accuracy of the test.

One convenient goal to quantify the diagnostic accuracy of a laboratory test is to express its performance by a single number. The most common global measure is the area under the ROC plot. By convention, this area is always $\geq 0.5$ (if it is not, one can reverse the decision rule to make it so). Values range between 1.0 (perfect separation of the test values of the two groups) and 0.5 (no apparent distributional difference between the two groups of test values). The area does not depend only on a particular portion of the plot such as the point closest to the diagonal or the sensitivity at 90% specificity, but on the entire plot. This is a quantitative, descriptive expression of how close the ROC plot is to the perfect one (area=1.0).

Combining measurements of ASC with other recently discovered markers, like CYFRA 21-1 or NMMT or with known markers like CEA and NSE, or with other markers of CRC yet to be discovered, leads and will lead, respectively, to further improvements in assessment of CRC.

The combination of the three markers ASC, CYFRA 21-1 and NSE significantly improves the diagnostic accuracy for CRC.

The following examples, references, sequence listing and figures are provided to aid the understanding of the present invention, the true scope of which is set forth in the appended claims. It is understood that modifications can be made in the procedures set forth without departing from the spirit of the invention.

| Abbreviations | |
|---|---|
| ABTS | 2,2'-azino-di- [3-ethylbenzthiazoline sulfonate (6)] diammonium salt |
| BSA | bovine serum albumin |
| cDNA | complementary DNA |
| CHAPS | (3-[(3-cholamidopropyl)-dimethylammonio]-1-propane-sulfonate) |
| DMSO | dimethyl sulfoxide |
| DTT | dithiothreitol |
| EDTA | ethylene diamine tetraacetic acid |
| ELISA | enzyme-linked immunosorbent assay |
| HRP | horseradish peroxidase |
| IAA | iodoacetamid |
| IgG | immunoglobulin G |
| IEF | isoelectric focussing |
| IPG | immobilized pH gradient |
| LDS | lithium dodecyl sulfate |
| MALDI-TOF | matrix-assisted laser desorption/ionisation-time of flight mass spectrometry |
| MES | mesityl, 2,4,6-trimethylphenyl |
| OD | optical density |
| PAGE | polyacrylamide gel electrophoresis |
| PBS | phosphate buffered saline |
| PI | isoelectric point |
| RTS | rapid translation system |
| SDS | sodium dodecyl sulfate |

SPECIFIC EMBODIMENTS

Example 1

Identification of ASC as a Potential Cancer Marker

Following an initial validation of ASC using samples of diseased and normal tissue from breast tumor patients the marker is tested for other cancers and particularly for colorectal cancer (see Table 6 below). In addition, serum and plasma samples from colorectal cancer patients are analyzed. As a result, for this type of cancer the data indicate the utility of ASC as a biochemical marker.

Example 2

Generation of Antibodies to the Marker Protein ASC

Polyclonal antibody to the cancer marker protein ASC is generated for further use of the antibody in the measurement of serum and plasma and blood levels of ASC by immunodetection assays, e.g. Western Blotting and ELISA Recombinant Protein Expression and Purification In order to generate antibodies to ASC, recombinant expression of the protein is performed for obtaining immunogens. The expression is done applying a combination of the RTS 100 expression system and E. coli. In a first step, the DNA sequence is analyzed and recommendations for high yield cDNA silent mutational variants and respective PCR-primer sequences are obtained using the ProteoExpert RTS E. coli HY system. Using the recommended primer pairs, the RTS 100 E. coli Linear Template Generation Set, His-tag (Roche Diagnostics GmbH, Mannheim, Germany, Cat. No. 3186237) system to generate linear PCR templates from the cDNA for in-vitro transcription and expression of the nucleotide sequence coding for the ASC protein is used. For Western-blot detection and later purification, the expressed protein contains a His-tag. The best expressing variant is identified. All steps from PCR to expression and detection are carried out according to the instructions of the manufacturer. The respective PCR product, containing all necessary T7 regulatory regions (promoter, ribosomal binding site and T7 terminator) is cloned into the pBAD TOPO vector (Invitrogen, Karlsruhe, Germany, Cat. No. K 4300/01) following the manufacturer's instructions. For expression using the T7 regulatory sequences, the construct is transformed into E. coli BL 21 (DE 3) (Studier, F. W., et al., Methods Enzymol. 185 (1990) 60-89) and the transformed bacteria are cultivated in a 1 l batch for protein expression.

Purification of His-ASC fusion protein is done following standard procedures on a Ni-chelate column. Briefly, 1 l of bacteria culture containing the expression vector for the His-ASC fusion protein is pelleted by centrifugation. The cell pellet is resuspended in lysis buffer, containing phosphate, pH 8.0, 7 M guanidium chloride, imidazole and thioglycerole, followed by homogenization using an ULTRA-TURRAX homogenizer (Ika-Werke GmbH). Insoluble material is pelleted by high speed centrifugation and the supernatant is applied to a Ni-chelate chromatographic column. The column is washed with several bed volumes of lysis buffer followed by washes with buffer, containing phosphate, pH 8.0 and urea. Finally, bound antigen is eluted using a phosphate buffer containing SDS under acid conditions.

Synthesis of Hemocyanin-Peptide-Conjugates for the Generation of Antibodies

Synthesis is carried out using heterobifunctional chemistry (maleimide/SH-chemistry). Selected cysteine containing ASC-peptides are coupled to 3-maleimidohexanoyl-N-hydroxysuccinimidester (MHS) activated hemocyanin from Concholepas concholepas (Sigma, B-8556).

Hemocyanin is brought to 10 mg/ml in 100 mM NaH$_2$PO$_4$/NaOH, pH 7.2. Per ml hemocyanin 100 µl MHS (12.3 mg in DMSO) are added and incubated for 1 h. The sample is dialyzed over night against 100 mM NaH$_2$PO$_4$/NaOH, pH 6.5 and adjusted to 6 mg/ml with dialysis buffer. A selected cysteine containing ASC-peptide was dissolved in DMSO (5 mg/ml for a peptide of 1500 Dalton). Per ml MHS-activated hemocyanin (6 mg/ml) 20 µl of 100 mM EDTA, pH 7.0 and 100 µl of the selected cysteine containing ASC-peptide are added. After 1 h the remaining maleimide groups are blocked by the addition of 10 µl 0.5 M cysteine/HCl per ml reaction mixture. This preparation is used for immunization without further purification.

Recombinant Fusion Protein Expression and Purification

In order to generate antibodies to ASC, recombinant expression of a SlyD-ASC fusion protein is performed to obtain immunogens, analogous to the method described by Scholz, C., et al., J. Mol. Biol. 345 (2005) 1229-1241. Therefore, an expression vector is constructed containing a gene encoding SlyD-(GGGS)$_5$-GGG-IEGR-ASC-GGGS-HHH-HHH ((GGGS)$_5$-GGG-IEGR and GGGS-HHHHHH disclosed as SEQ ID NO'S 6-7 respectively). For purification and Western blot detection, the construct contains a carboxy-terminal His-Tag (HHHHHH) (SEQ ID NO: 8). An additional GS-Linker ((GGGS)$_5$-GGG) (SEQ ID NO: 9) and a cleavage site for Factor Xa (IEGR) (SEQ ID NO: 10) is inserted between SlyD and ASC. Expression is done in *E. coli* under control of the T5-promoter.

In a first step, PCR is done using the vector pSO60 (pET24 carrying an expression cassette encoding SlyD-(GGGS)$_5$-GGG-SlyD) ((GGGS)$_5$-GGG disclosed as SEQ ID NO: 9) as a template. By use of primer 1 (SEQ ID NO: 2) and primer 2 (SEQ ID NO: 3), monoSlyD is obtained carrying an EcoRI-site and a ribosomal binding site at the 5'-end and a BamHI-site, the IEGR-encoding sequence and a SacI-site at the 3'-end, respectively. The generated PCR-product is cloned as a EcoRI/SacI-fragment into pQE80L (Qiagen, Hilden) giving pQE80-SlyD.

Secondly, ASC is amplified from pBC14 (pET24 carrying ASC) as the template. By use of primer 3 (SEQ ID NO: 4) and primer 4 (SEQ ID NO: 5), a BamHI-site and an IEGR-encoding sequence at the 5'-end as well as a GGGS-HHHHHH-encoding sequence (SEQ ID NO: 7) and an additional HindIII-site at the 3'-end are inserted.

This PCR-product is cloned as a BamHI/HindIII fragment into pQE80-SlyD resulting in the final expression construct (pQE80-SlyD-ASC). All PCR- and cloning-steps are performed according to the manufacturer's instructions.

For expression under control of the T5 promoter, *E. coli* C600 cells (Stratagene, Heidelberg) are transformed with the final construct. Expression strains are cultivated in a 1 l batch for protein production.

Purification of His-SlyD-ASC fusion protein is done following standard procedures on a Ni-chelate column. Briefly, 1 liter of bacteria culture containing the expression vector for the SlyD-ASC-His-fusion protein is pelleted by centrifugation. The cell pellet is resuspended in lysis buffer containing Tris/HCl, pH 8, CHAPS, EDTA und lysozyme, followed by homogenization using an ULTRA-TURRAX. DNA is enzymatically degraded by the addition of magnesium chloride and DNase. The inclusion bodies are pelleted by centrifugation. The pellet is dissolved in phosphate buffer, pH 8.0, 7 M guanidinium chloride and loaded on a Ni-chelate column. The column is washed with several bed volumes phosphate buffer, pH 8.0, 7 M guanidinium chloride. Then, the phosphate buffer, pH 8.0, 7 M guanidinium chloride is replaced by phosphate buffer, pH 8.0, NaCl to induce refolding of the matrix bound protein. The refolded fusion protein is eluted by phosphate buffer, pH 8.0, NaCl, imidazole.

Production of Monoclonal Antibodies Against ASC a) Immunization of Mice 12 week old A/J mice are initially immunized intraperitoneally with 100 µg ASC, fusion protein or hemocyanin-peptide-conjugate (see above). This is followed after 6 weeks by two further intraperitoneal immunizations at monthly intervals. In this process each mouse is administered 100 µg ASC or hemocyanin-peptide-conjugate adsorbed to aluminum hydroxide and $10^9$ germs of *Bordetella pertussis*. Subsequently the last two immunizations are carried out intravenously on the 3rd and 2nd day before fusion using 100 µg ASC or hemocyanin-peptide-conjugate in PBS buffer for each.

b) Fusion and Cloning

Spleen cells of the mice immunized according to a) are fused with myeloma cells according to Galfre, G., and Milstein, C., Methods in Enzymology 73 (1981) 346. In this process ca. $1 \times 10^8$ spleen cells of the immunized mouse are mixed with $2 \times 10^7$ myeloma cells (P3X63-Ag8-653, ATCC CRL1580) and centrifuged (10 min at 300×g and 4° C.). The cells are then washed once with RPMI 1640 medium without foetal calf serum (FCS) and centrifuged again at 400×g in a 50 ml conical tube. The supernatant is discarded, the cell sediment is gently loosened by tapping, 1 ml PEG (molecular weight 4000, Merck, Darmstadt) is added and mixed by pipetting. After 1 min in a water-bath at 37° C., 5 ml RPMI 1640 without FCS is added drop-wise at room temperature within a period of 4-5 min. Afterwards 5 ml RPMI 1640 containing 10% FCS is added drop-wise within ca. 1 min, mixed thoroughly, filled to 50 ml with medium (RPMI 1640+10% FCS) and subsequently centrifuged for 10 min at 400×g and 4° C. The sedimented cells are taken up in RPMI 1640 medium containing 10% FCS and sown in hypoxanthine-azaserine selection medium (100 mmol/l hypoxanthine, 1 µg/ml azaserine in RPMI 1640+10% FCS). Interleukin 6 at 100 U/ml is added to the medium as a growth factor.

After ca. 10 days the primary cultures are tested for specific antibody. ASC-positive primary cultures are cloned in 96-well cell culture plates by means of a fluorescence activated cell sorter. In this process again interleukin 6 at 100 U/ml is added to the medium as a growth additive.

c) Immunoglobulin Isolation from the Cell Culture Supernatants

The hybridoma cells obtained are sown at a density of $1 \times 10^5$ cells per ml in RPMI 1640 medium containing 10% FCS and proliferated for 7 days in a fermenter (Thermodux Co., Wertheim/Main, Model MCS-104XL, Order No. 144-050). On average concentrations of 100 µg monoclonal antibody per ml are obtained in the culture supernatant. Purification of this antibody from the culture supernatant is carried out by conventional methods in protein chemistry (e.g. according to Bruck, C., et al., Methods in Enzymology 121 (1986) 587-695).

Generation of Polyclonal Antibodies a) Immunization

For immunization, a fresh emulsion of the protein solution (100 µg/ml ASC, fusion protein or hemocyanin-peptide-conjugate) and complete Freund's adjuvant at the ratio of 1:1 is prepared. Each rabbit is immunized with 1 ml of the emulsion at days 1, 7, 14 and 30, 60 and 90. Blood is drawn and resulting anti-ASC serum used for further experiments as described in Examples 3 and 4.

b) Purification of IgG (Immunoglobulin G) from Rabbit Serum by Sequential Precipitation with Caprylic Acid and Ammonium Sulfate One volume of rabbit serum is diluted with 4 volumes of acetate buffer (60 mM, pH 4.0). The pH is adjusted to 4.5 with 2 M Tris-base. Caprylic acid (25 µl/ml of diluted sample) is added drop-wise under vigorous stirring. After 30 min the sample is centrifuged (13,000×g, 30 min, 4° C.), the pellet discarded and the supernatant collected. The pH of the supernatant is adjusted to 7.5 by the addition of 2 M Tris-base and filtered (0.2 µm).

The immunoglobulin in the supernatant is precipitated under vigorous stirring by the drop-wise addition of a 4 M ammonium sulfate solution to a final concentration of 2 M. The precipitated immunoglobulins are collected by centrifugation (8,000×g, 15 min, 4° C.).

The supernatant is discarded. The pellet is dissolved in 10 mM $NaH_2PO_4$/NaOH, pH 7.5, 30 mM NaCl and exhaustively dialyzed. The dialysate is centrifuged (13,000×g, 15 min, 4° C.) and filtered (0.2 µm).

Biotinylation of Polyclonal Rabbit IgG

Polyclonal rabbit IgG is brought to 10 mg/ml in 10 mM $NaH_2PO_4$/NaOH, pH 7.5, 30 mM NaCl. Per ml IgG solution 50 µl Biotin-N-hydroxysuccinimide (3.6 mg/ml in DMSO) are added. After 30 min at room temperature, the sample is chromatographed on SUPERDEX 200 (GE Healthcare Bio-Sciences AB) (10 mM $NaH_2PO_4$/NaOH, pH 7.5, 30 mM NaCl). The fraction containing biotinylated IgG are collected. Monoclonal antibodies are biotinylated according to the same procedure.

Digoxygenylation of Polyclonal Rabbit IgG

Polyclonal rabbit IgG is brought to 10 mg/ml in 10 mM $NaH_2PO_4$/NaOH, 30 mM NaCl, pH 7.5. Per ml IgG solution 50 µl digoxigenin-3-O-methylcarbonyl-ε-aminocaproic acid-N-hydroxysuccinimide ester (Roche Diagnostics, Mannheim, Germany, Cat. No. 1 333 054) (3.8 mg/ml in DMSO) are added. After 30 min at room temperature, the sample is chromatographed on SUPERDEX 200 (10 mM $NaH_2PO_4$/NaOH, pH 7.5, 30 mM NaCl). The fractions containing digoxigenylated IgG are collected. Monoclonal antibodies are labeled with digoxigenin according to the same procedure.

Example 3

Western Blot for the Detection of ASC in Human Serum and Plasma Samples

SDS-PAGE and Western Blotting are carried out using reagents and equipment of Invitrogen, Karlsruhe, Germany. Human plasma samples are diluted 1:20 in reducing NUPAGE (Invitrogen Corporation) LDS sample buffer and heated for 5 min at 95° C. 10 µl aliquots are run on 4-12% NUPAGE gels (Bis-Tris) in the MES running buffer system. The gel-separated protein mixture is blotted onto nitrocellulose membranes using the Invitrogen XCell II™ Blot Module (Invitrogen) and the NUPAGE transfer buffer system. The membranes are washed 3 times in PBS/0.05% TWEEN 20 (ICI Americas Inc.) and blocked with SuperBlock Blocking Buffer (Pierce Biotechnology, Inc., Rockford, Ill., USA). The biotinylated primary antibody is diluted in SuperBlock Blocking Buffer (0.01-0.2 µg/ml) and incubated with the membrane for 1 h. The membranes are washed 3 times in PBS/0.05% TWEEN 20. The specifically bound biotinylated primary antibody is labeled with a streptavidin-HRP-conjugate (20 $mU_{ABTS}$/ml in SuperBlock Blocking Buffer). After incubation for 1 h, the membranes are washed 3 times in PBS/0.05% TWEEN 20. The bound streptavidin-HRP-conjugate is detected using a chemiluminescent substrate (SuperSignal West Femto Substrate, Pierce Biotechnology, Inc., Rockford, Ill., USA) and autoradiographic film. Exposure times varies from 10 min to over night.

Example 4

ELISA for the Measurement of ASC in Human Serum and Plasma Samples

For detection of ASC in human serum or plasma, a sandwich ELISA is developed. For capture and detection of the antigen, aliquots of the anti-ASC polyclonal antibody (see Example 2) are conjugated with biotin and digoxygenin, respectively.

Streptavidin-coated 96-well microwell plates are incubated with 100 µl biotinylated anti-ASC polyclonal antibody for 60 min at 10 µg/ml in 10 mM phosphate, pH 7.4, 1% BSA, 0.9% NaCl and 0.1% TWEEN 20. After incubation, plates are washed three times with 0.9% NaCl, 0.1% TWEEN 20. Wells are then incubated for 2 h with either a serial dilution of the recombinant protein (see Example 2) as standard antigen or with diluted liquid samples obtained from patients. After binding of ASC, plates are washed three times with 0.9% NaCl, 0.1% TWEEN 20. For specific detection of bound ASC, wells are incubated with 100 µl of digoxygenylated anti-ASC polyclonal antibody for 60 min at 10 µg/ml in 10 mM phosphate, pH 7.4, 1% BSA, 0.9% NaCl and 0.1% TWEEN 20. Thereafter, plates are washed three times to remove unbound antibody. In a next step, wells are incubated with 20 mU/ml anti-digoxigenin-POD conjugates (Roche Diagnostics GmbH, Mannheim, Germany, Catalog No. 1633716) for 60 min in 10 mM phosphate, pH 7.4, 1% BSA, 0.9% NaCl and 0.1% TWEEN 20. Plates are subsequently washed three times with the same buffer. For detection of antigen-antibody complexes, wells are incubated with 100 µl ABTS solution (Roche Diagnostics GmbH, Mannheim, Germany, Catalog No. 11685767) and OD is measured after 30-60 min at 405 nm with an ELISA reader.

Example 5

Marker Evaluation, Sensitivity and Specificity

ROC Analysis to Assess Clinical Utility in Terms of Diagnostic Accuracy

Accuracy is assessed by analyzing individual liquid samples obtained from well-characterized patient cohorts. The control collective A (see Table 1) contains 317 individuals comprising 271 blood donors and 46 patients having undergone coloscopy. Control collective B comprises 87 patients with non-cancerous diseases.

The 109 colorectal cancer patients (collective C) comprise tumors of different stages (Table 2, Table 4). Furthermore, 27 samples at a precancerous stage are included in the analysis (collective D). To analyze the specificity with regard to other cancers 272 patients with other tumors (collective E) are included into the sample cohort. The cohort is summarized in Tables 2; Table 3 provides details for the patients with gastrointestinal cancers.

CA 19-9, CYFRA 21-1 and CEA are measured by commercially available assays (Roche Diagnostics, CA 19-9-assay: Cat. No. 11776193, CYFRA 21-1 assay Cat. No. 11820966, CEA-assay: Cat. No. 1731629) for Elecsys® Systems immunoassay analyzer). NNMT is measured using the procedure of Example 4 and antibodies as described in WO 2004/057336. An in-house sandwich immunoassay has been developed for measurement of ASC. This assay is performed in a microtiter plate format. Streptavidin-coated microtiter plates are used. A biotinylated polyclonal antibody to ASC is used as a capturing antibody and a digoxigenylated polyclonal antibody to ASC is used as the second specific binding partner in this sandwich assay. The sandwich complex formed is finally visualized by an anti-digoxigenin horseradish peroxidase conjugate and an appropriate peroxidase substrate.

TABLE 1

Patient collective, controls

| | | |
|---|---|---|
| A) Healthy patients Σ | | 317 |
| | Blood donors, 30-40 years old | 150 |
| | Blood donors, age-matched | 121 |
| | Coloscopy-negative controls | 46 |
| B) Disease controls Σ | | 87 |
| | Diverticulosis | 50 |
| | Diverticulitis | 7 |
| | Colitis | 12 |
| | Inflammatory bowel disease (Morbus Crohn, ulcerative colitis, inflammatory relapsing diarrhea) | 10 |
| | Ulcer | 3 |
| | Other bowel diseases | 5 |

TABLE 2

Patient collective, cancer patients

| | | |
|---|---|---|
| C) Colorectal cancer patients, total | | 109 |
| | Collective (a) | 69 |
| | Collective (b) | 40 |
| D) Precancerous stage | Collective (c), adenoma <1 cm; precancerous | 27 |
| E) Other cancer patients, total | | 272 |
| | Non-CRC gastrointestinal cancers | 21] |
| | Gynecological cancers | 71 |
| | Breast cancers | 90 |
| | Lung cancer | 20 |
| | Prostate cancer | 51 |
| | Bladder cancer | 19 |
| | Other cancers | 1 |

TABLE 3

Patient collective, patients with other GI cancers

| | |
|---|---|
| Total | 21 |
| Stomach cancer | 20 |
| Pancreas cancer | 1 |

TABLE 4

Colorectal cancer - stages of disease

| | |
|---|---|
| Total | 109 |
| UICC 0 | 3 (3%) |
| UICC I | 33 (30%) |
| UICC II | 23 (21%) |
| UICC III | 21 (19%) |
| UICC IV | 23 (21%) |
| Unknown stages | 6 (6%) |

Figure 2:
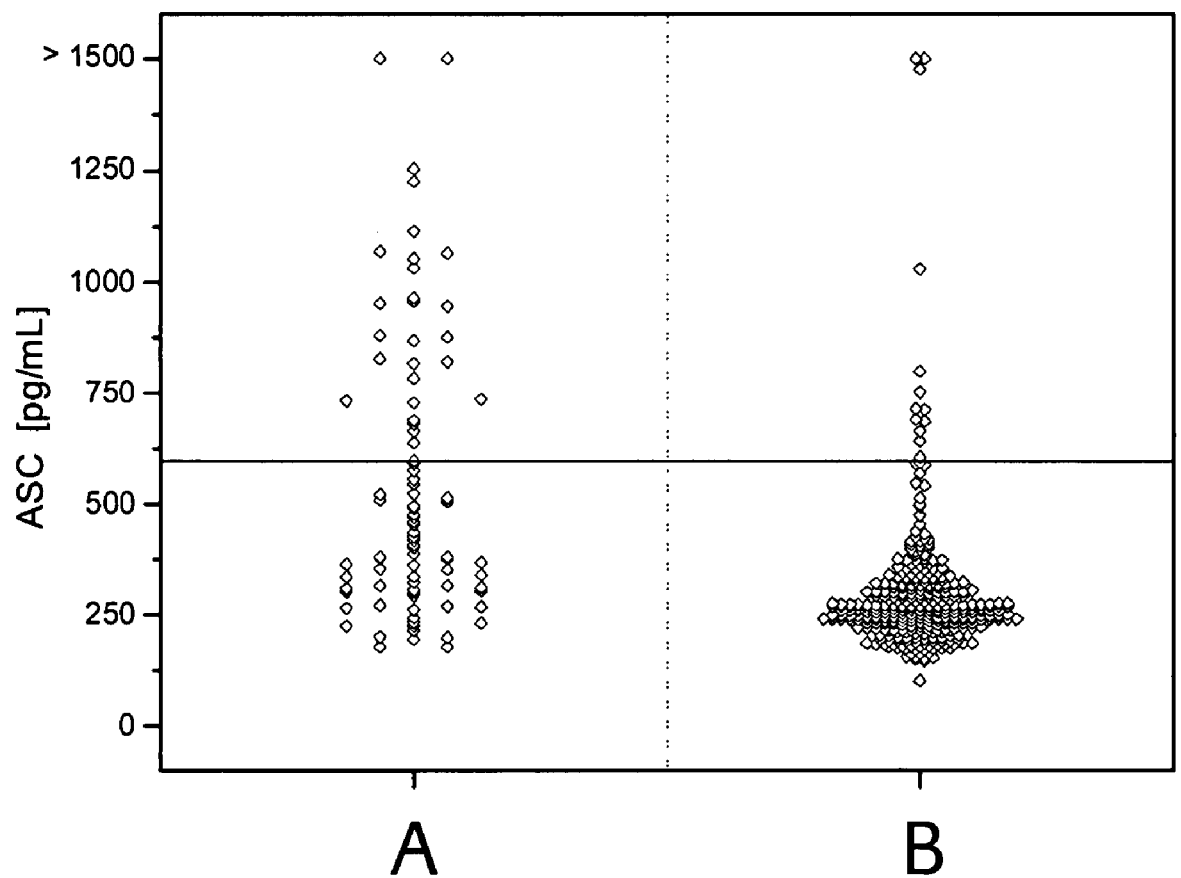
FIG. 2 Distribution of ASC quantification in serum and plasma samples (see Example 4) of control patients according to Table 1. A: disease controls, n=87; B: healthy controls, n=317. The horizontal line in the diagram indicates the cutoff value of 597 pg/ml.

FIG. 2 summarizes the data obtained with the control (Table 1) serum and plasma samples. The figure shows that more samples of the disease controls than of the healthy controls exhibit high ASC values. Taking this finding into account the cutoff value is defined as defining the 90% percentile of all controls, that is to say healthy and disease controls.

With specific regard to the disease controls Table 5 compares the specificity of the marker ASC with the specificities of NNMT, CA 19-9, CEA and CYFRA 21-1. As for ASC, the cutoff value of each other marker defines the 90% percentile of all controls.

TABLE 5

Specificity of ASC and other tumor markers in disease controls (patient collective B)

| | Number of patients | ASC | NNMT | CA 19-9 | CEA | CYFRA 21-1 |
|---|---|---|---|---|---|---|
| All disease controls | 87 | 67.8% | 75.9% | 85.1% | 83.9% | 80.5% |
| Diverticulosis | 50 | 76% | 76% | 82% | 80% | 82% |
| Diverticulitis | 7 | 43% | 57% | 100% | 86% | 100% |
| Colitis | 12 | 58% | 67% | 92% | 83% | 75% |
| CED | 10 | 70% | 90% | 80% | 100% | 70% |

The specificity of ASC is assessed by testing serum and plasma samples from patients diagnosed with other cancers. Specificity is compared with respect to the other markers used. Table 6 summarizes the results.

TABLE 6

Specificity of ASC and other tumor markers with regard to other cancers (patient collective E)

| | Number of patients | ASC | NNMT | CA 19-9 | CEA | CYFRA 21-1 |
|---|---|---|---|---|---|---|
| All other cancers tested | 272 | 57.7% | 76.1% | 81.6% | 82.4% | 62.9% |
| Breast | 90 | 58% | 89% | 87% | 83% | 71% |
| Stomach | 20 | 35% | 45% | 60% | 75% | 15% |
| Ovary | 28 | 46% | 50% | 68% | 82% | 18% |
| Endometrium | 27 | 67% | 74% | 81% | 93% | 89% |
| Cervix | 12 | 67% | 67% | 75% | 83% | 75% |
| Lung | 20 | 10% | 40% | 95% | 60% | 25% |
| Bladder | 19 | 68% | 89% | 95% | 95% | 89% |
| Prostate | 51 | 80% | 96% | 82% | 84% | 82% |

Figure 3:
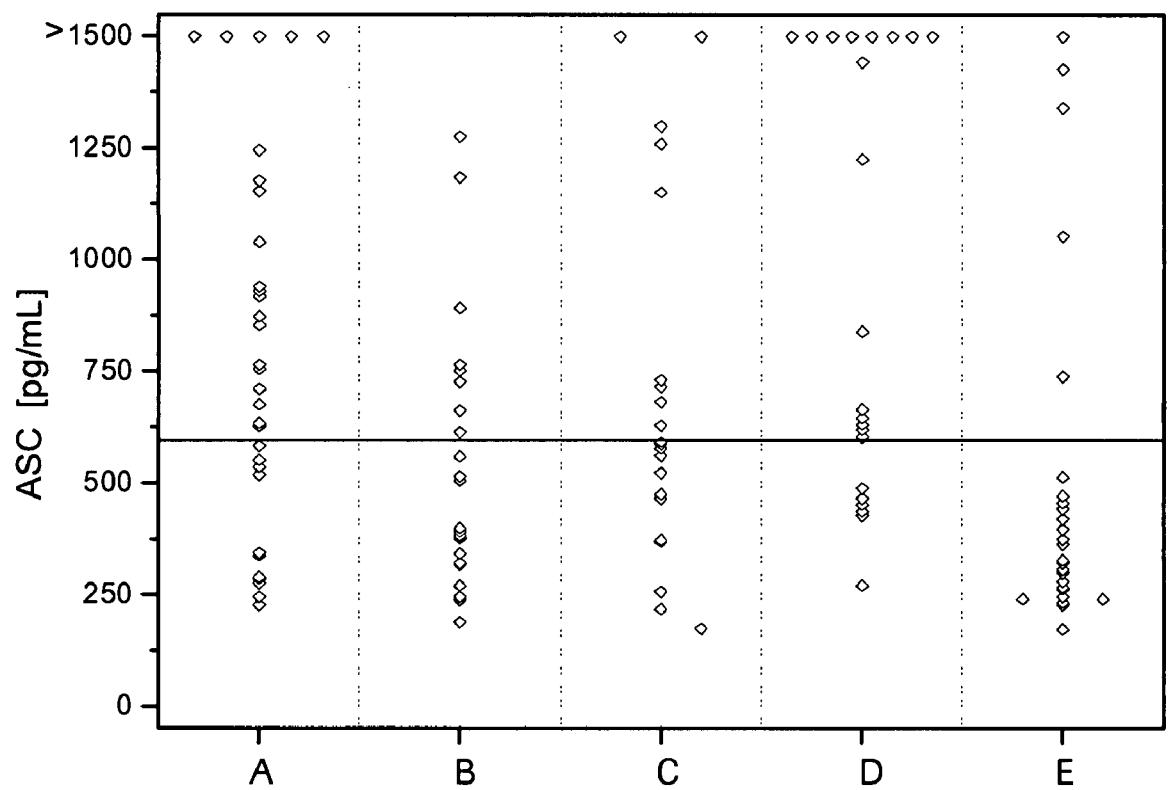
FIG. 3 Distribution of measured values for ASC. The cutoff line corresponds to 597 pg/ml and a specificity of 90% with respect to the collective of control patients (Table 1). A: UICC I, n=33; B: UICC II, n=23; C: UICC III, n=21; D: UICC IV, n=23; E: Adenoma, n=27.
Figure 4:
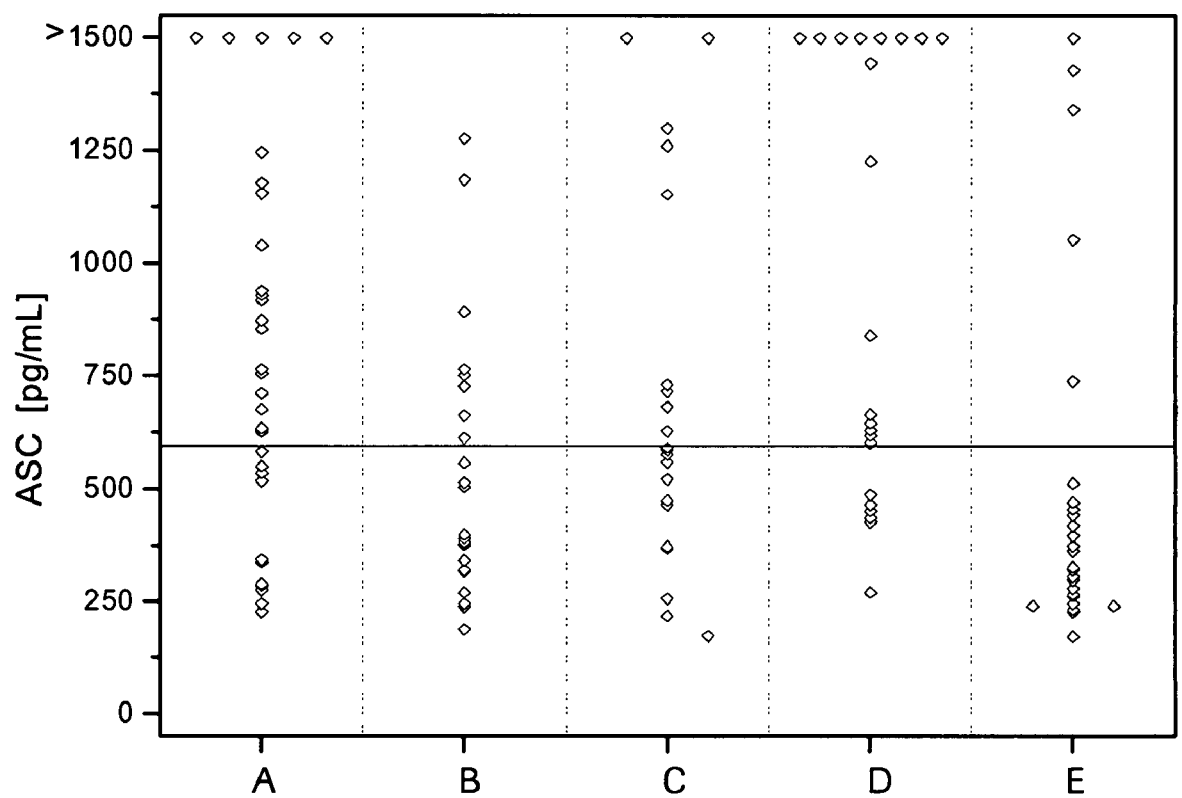
FIG. 4 Distribution of measured values for CEA. The cutoff line corresponds to 4 ng/ml and a specificity of 90% with respect to the collective of control patients (Table 1). A: UICC I, n=33; B: UICC II, n=23; C: UICC III, n=21; D: UICC IV, n=23; E: Adenoma, n=28.

To evaluate sensitivity with respect to ASC, serum and plasma samples from patients diagnosed with CRC at different stages are analyzed. Tables 7a/b and 8 summarize the results. The distributions of measured values for ASC and CEA are shown on in FIG. 3 and FIG. 4, respectively.

TABLE 7a

Sensitivity with respect to colorectal cancer

| | Number of patients | ASC | NNMT | CA 19-9 | CEA | CYFRA 21-1 |
|---|---|---|---|---|---|---|
| UICC 0 | 3 | 100% | 67% | 33% | 67% | 33% |
| UICC I | 33 | 67% | 52% | 18% | 39% | 55% |
| UICC II | 23 | 35% | 26% | 30% | 22% | 43% |
| UICC III | 21 | 43% | 67% | 38% | 48% | 71% |
| UICC IV | 23 | 74% | 74% | 57% | 83% | 74% |
| Without staging | 6 | 0% | 67% | 0% | 33% | 33% |
| CRC patients tested | 109 | 54.1% | 55.0% | 32.1% | 46.8% | 57.8% |

TABLE 7b

Sensitivity with respect to precancerous stage

| | Number of patients | ASC | NNMT | CA 19-9 | CEA | CYFRA 21-1 |
|---|---|---|---|---|---|---|
| Adenoma >1 cm | 27 | 18.5% | 22.2% | 11.1% | 25.9% | 25.9% |

Figure 5:
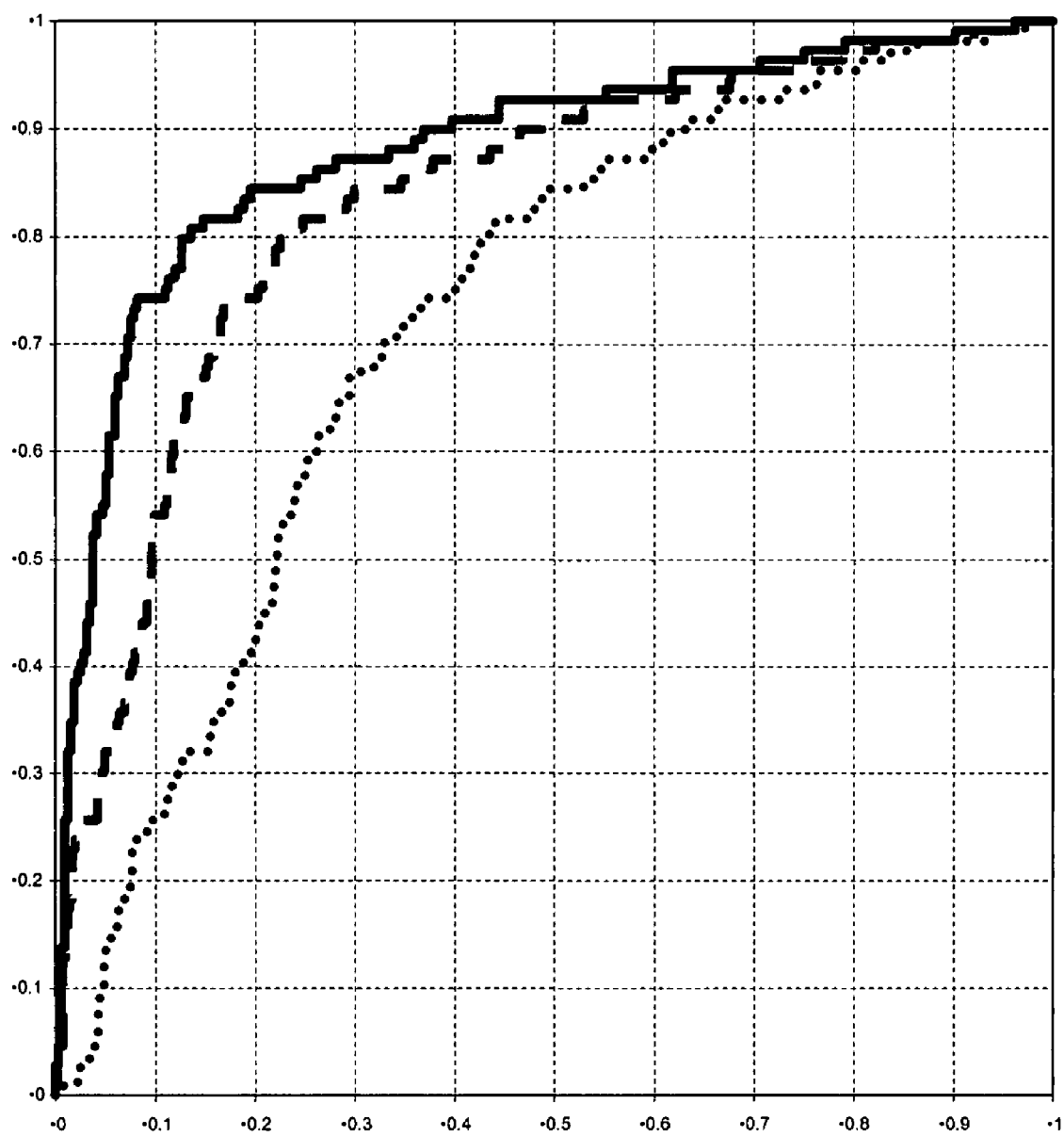
FIG. 5 The figure shows ROC curves for ASC: Colorectal cancer versus healthy controls (solid line; ROC: 88%), colorectal cancer versus healthy controls and disease controls (dashed line; ROC: 83%) and colorectal cancer versus healthy controls, disease controls and other cancers. The x-axis indicates the value computed by subtracting from 1 the specificity value. The y-axis indicates sensitivity. In both, the value of 1 corresponds to 100%. Colorectal cancer: 109 samples. Healthy controls: 317 samples. Disease controls: 87 samples. Other cancers: 272 samples.
Figure 6:
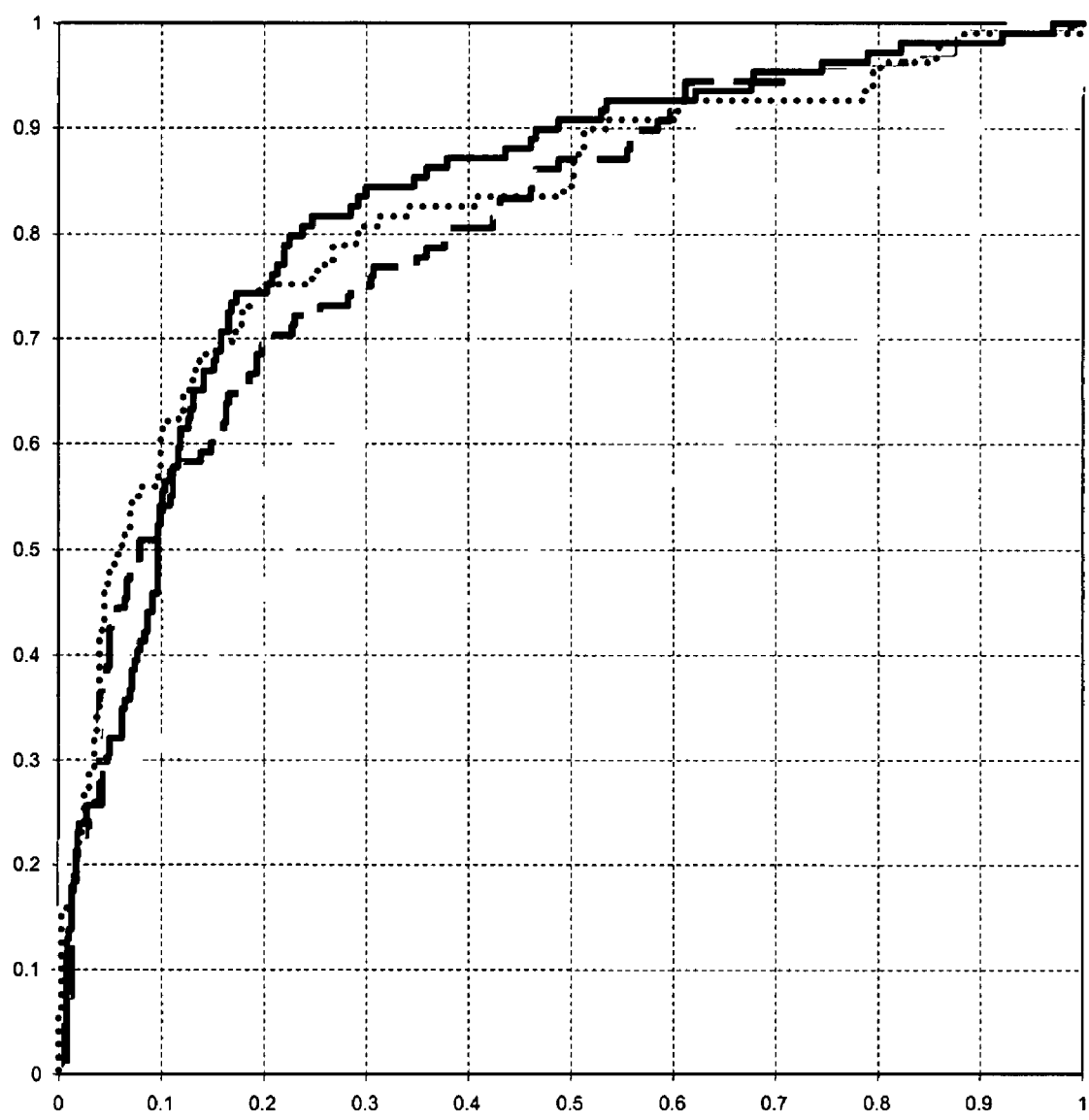
FIG. 6 The figure shows ROC curves for ASC, CYFRA 21-1 and NNMT: Colorectal cancer versus healthy controls and disease controls. ASC is indicated by the solid line, CYFRA 21-1 by the dotted line and NNMT by the dashed line. The x-axis indicates the value computed by subtracting from 1 the specificity value. The y-axis indicates sensitivity. In both the value of 1 corresponds to 100%. Colorectal cancer: 109 samples. Healthy controls: 317 samples. Disease controls: 87 samples. Other cancers: 272 samples.
Figure 7:
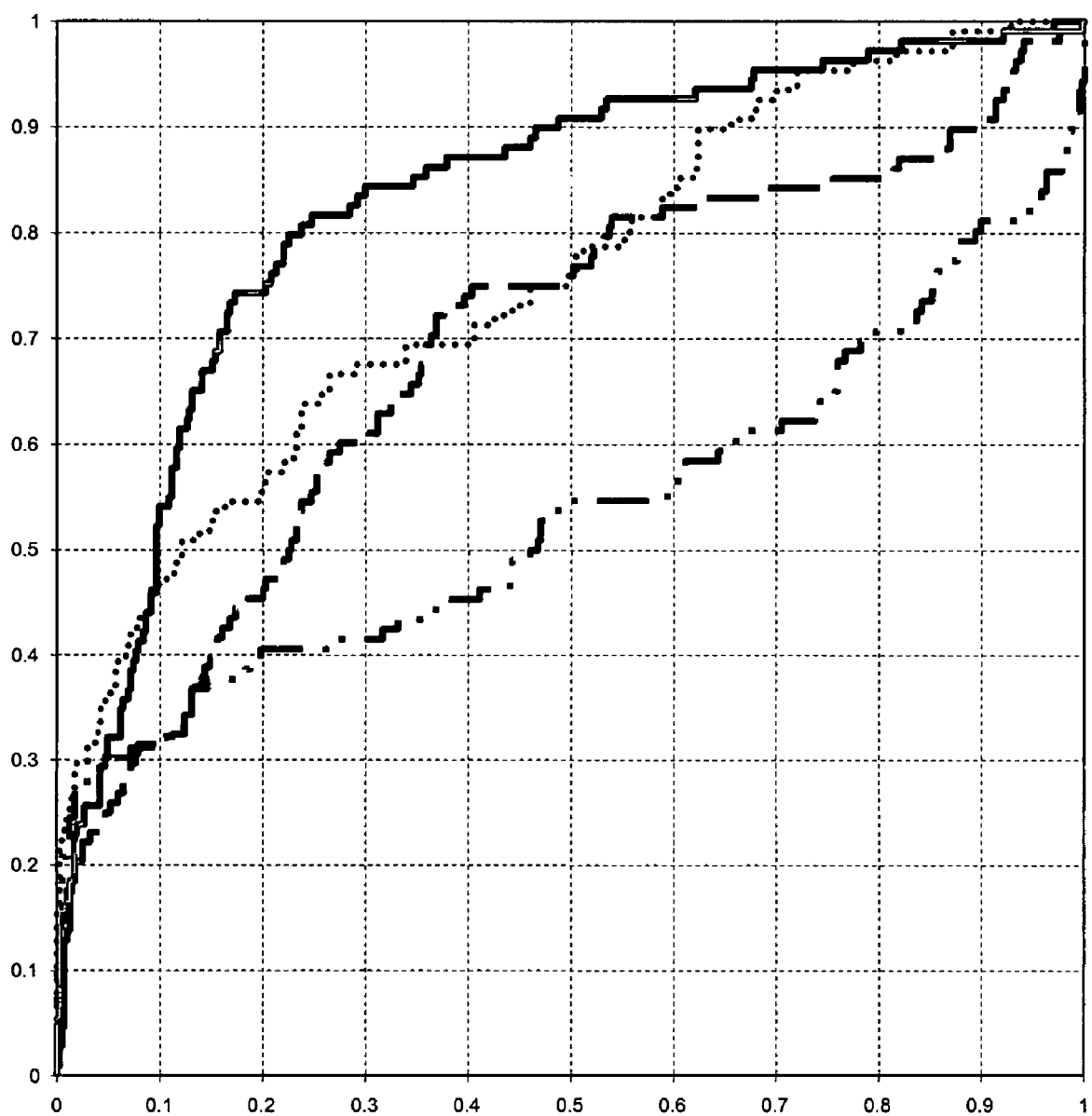
FIG. 7 The figure shows ROC curves for ASC, CEA, CA 19-9 and NSE: Colorectal cancer versus healthy controls and disease controls. ASC is indicated by the solid line, CEA by the dotted line, CA 19-9 by the dashed line, NSE by the patchy dashed line. The x-axis indicates the value computed by subtracting from 1 the specificity value. The y-axis indicates sensitivity. In both the value of 1 corresponds to 100%. Colorectal cancer: 109 samples. Healthy controls: 317 samples. Disease controls: 87 samples. Other cancers: 272 samples.

ROC analysis is performed according to Zweig, M. H., and Campbell, supra. Discriminatory power for differentiating patients in the colorectal cancer group from the healthy control group as measured by the area under the curve (AUC) is found to be at least as good or even better for ASC (88%) as compared to the other markers tested. When the colorectal cancer collective is compared with all controls including the disease controls, the discriminatory power of ASC is still at least equal to, if not better than, the marker CYFRA 21-1. In addition, discriminatory power of ASC is notably better than that of NNMT. The results are given by Table 8 and FIGS. 5 and 6.

TABLE 8

ROC analysis

| | ASC | NNMT | CA 19-9 | CEA | CYFRA 21-1 |
|---|---|---|---|---|---|
| Colon Cancer/Healthy Controls | 88% | 84% | 72% | 77% | 84% |
| Colon Cancer/Healthy Controls + Disease Controls | 83% | 80% | 70% | 75% | 82% |
| Colon Cancer/Healthy Controls + Disease Controls + Other Cancers | 72% | 75% | 66% | 73% | 75% |

As becomes clear from the data shown, apart from indicating tumors ASC is also elevated in bowel disease controls. In spite of the lower specificity to bowel disease controls the differentiation between colon cancer samples and controls (healthy+disease) is better than for the routine tumor markers CEA and CA 19-9.

Example 6

Marker Panel

As shown in Example 5, ASC is a promising candidate for evaluation as a member in a colon marker panel, that is in combination with one or more other markers. To this end, a preliminary multivariate analysis is carried out.

The classification algorithms are generated with the Regularized Discriminant Analysis (RDA), which is a generalization of the common Discriminant Analysis, i.e. Quadratic- and Linear Discriminant Analysis (McLachlan, G. J., Discriminant Analysis and Statistical Pattern Recognition, Wiley Series in probability and mathematical statistics, 1992). In the RDA alternatives to the usual maximum likelihood (plug-in) estimates for the covariance matrices are used. These alternatives are characterized by two parameters ($\lambda$, $\gamma$), the values of which are customized to individual situations by jointly minimizing a sample-based estimate of future misclassification risk (Friedman, J. H., Regularized Discriminant Analysis, J. of the American Statistical Association 84 (1989) 165-175). As an alternative method Support Vector Machines algorithms (Hastie, Trevor, Tibshirani, Robert, Friedman, Jerome, The Elements of Statistical Learning, Springer Series in Statistics, 2001) can be fitted with comparable classification results. Analysis by RDA is based on 106 CRC samples and 404 healthy/disease controls.

The marker panels are stepwise constructed starting from the best single marker for the classification problem and ending when the increase in the sensitivity at a specificity level of 90% does not change remarkably any more. In order to gain centralized distributions every single marker is transformed with the natural logarithmic (log) function.

Table 9 presents the RDA data obtained using a comparison of CRC samples versus healthy/disease control samples with the specificity being set to 90%. It is noted that ASC has the best ROC area under the curve of all tumor markers tested.

TABLE 9

| Univariate analysis | | |
| --- | --- | --- |
| Marker | ROC-AUC | Sensitivity |
| CEA | 0.75 | 47.2% |
| CA 15-3 | 0.53 | 15.1% |
| CA 125 | 0.63 | 26.4% |
| CA 19-9 | 0.70 | 31.1% |
| CA 72-4 | 0.64 | 26.4% |
| CYFRA 21-1 | 0.82 | 60.4% |
| NSE | 0.54 | 31.1% |
| AFP | 0.50 | 11.3% |
| NNMT | 0.80 | 52.8% |
| ASC | 0.83 | 54.7% |

Tables 10 and 11 display the results from multivariate analysis. Surprisingly, the search for the best combination of 2, 3, 4, and 5 different markers leads to the observation that combinations including CEA (and also CA 19-9) appear to be inferior. The best combination found on the basis of the present sample set includes CYFRA 21-1, NSE and ASC. This result is exemplarily illustrated by Table 11 which reflects the results with different combinations including CEA.

TABLE 10

| | | | Multivariate analysis (1) | | |
| --- | --- | --- | --- | --- | --- |
| | | | | Cross-validation (5-fold) | |
| Number of markers | Panel of markers | Method (RDA) | Error total | Sensitivity | Specificity |
| 1 | log_CYFRA 21-1 | $\lambda = 0.25$; $\gamma = 0$ | 0.16322 | 59.7% | 90.3% |
| 2 | log_CYFRA 21-1, log_NSE | $\lambda = 0$; $\gamma = 0.75$ | 0.14052 | 69.6% | 90.5% |
| 3 | log_CYFRA 21-1, log_NSE, log_ASC | $\lambda = 0.5$; $\gamma = 0$ | 0.12260 | 78.7% | 90.2% |
| 4 | log_CYFRA 21-1, log_NSE, log_ASC, log_NNMT | $\lambda = 0.5$; $\gamma = 0$ | 0.12807 | 76.4% | 90% |
| 5 | log_CYFRA 21-1, log_NSE, log_ASC, log_NNMT, log_AFP | $\lambda = 0.75$; $\gamma = 0$ | 0.13192 | 74.7% | 90% |

TABLE 11

Multivariate analysis (2); preselected markers ASC, NNMT, CEA

| Number of markers | Panel of markers | Method (RDA) | Cross-validation (5-fold) | | |
|---|---|---|---|---|---|
| | | | Error total | Sensitivity | Specificity |
| 2 | log_ASC, log_CEA | $\lambda = 0.25$; $\gamma = 0.25$ | 0.16287 | 58% | 90.6% |
| 2 | log_NNMT, log_CEA | $\lambda = 0.5$; $\gamma = 0$ | 0.16175 | 59.3% | 90.3% |
| 3 | log_NNMT, log_CEA, log_ASC | $\lambda = 1$; $\gamma = 0.25$ | 0.15828 | 61.8% | 90.1% |

What is claimed is:

1. A method for assessing colorectal cancer in a patient comprising the steps of:
measuring in a sample from the patient a concentration of apoptosis-associated speck-like protein containing a caspase-associated recruitment domain (ASC, SEQ ID NO: 1),
comparing the concentration of ASC measured with a level of ASC in individuals without colorectal cancer and using the comparison to assess colorectal cancer in the patient, wherein if the concentration of ASC measured is greater than the level of ASC in individuals without colorectal cancer, colorectal cancer is assessed as indicated in the patient.

2. The method of claim 1 wherein the sample is selected from the group consisting of serum, plasma, and whole blood.

3. The method of claim 1 further comprising the step of measuring in the sample a concentration of a marker selected from the group consisting of neuron-specific enolase (NSE), soluble fragment of cytokeratin 19 (CYFRA 21-1), nicotinamide N-methyltransferase (NNMT), carbohydrate antigen 19-9 (CA 19-9), carbohydrate antigen 72-4 (CA 72-4), and carcinoembryonic antigen (CEA) and including the concentration of the marker in the comparison step.

4. The method of claim 3 wherein the marker is CYFRA 21-1.

5. The method of claim 3 wherein the marker is NSE.

6. A method for assessing colorectal cancer in a patient comprising the steps of:
combining a sample from the patient with a specific binding agent for apoptosis-associated speck-like protein containing a caspase-associated recruitment domain (ASC, SEQ ID NO: 1) under conditions whereby a complex is formed between the binding agent and ASC,
measuring an amount of the complex formed, and
comparing the measured amount of complex formed with a control amount derived from patients without colorectal cancer, wherein the assessment indicates colorectal cancer where the measured amount is greater than the control amount.

7. The method of claim 6 wherein the sample is also combined with a specific binding agent for a marker selected from the group consisting of neuron-specific enolase (NSE), soluble fragment of cytokeratin 19 (CYFRA 21-1), nicotinamide N-methyltransferase (NNMT), carbohydrate antigen 19-9 (CA 19-9), carbohydrate antigen 72-4 (CA 72-4), and carcinoembryonic antigen (CEA) under conditions whereby a complex is formed between the binding agent specific for the marker and the marker and wherein the amount of said complex is included in the comparison step.

8. The method of claim 7 wherein the marker is CYFRA 21-1.

9. The method of claim 7 wherein the marker is NSE.

* * * * *